(12) United States Patent
Vandyck et al.

(10) Patent No.: US 10,941,113 B2
(45) Date of Patent: *Mar. 9, 2021

(54) SULFAMOYL-ARYLAMIDES AND THE USE THEREOF AS MEDICAMENTS FOR THE TREATMENT OF HEPATITIS B

(71) Applicant: Janssen Sciences Ireland UC, Little Island, Co Cork (IE)

(72) Inventors: Koen Vandyck, Paal-Beringen (BE); Stefaan Julien Last, Beveren (BE); Pierre Jean-Marie Bernard Raboisson, Wavre (BE)

(73) Assignee: Janssen Sciences Ireland UC, Little Island (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/188,238

(22) Filed: Nov. 12, 2018

(65) Prior Publication Data

US 2019/0077749 A1   Mar. 14, 2019

Related U.S. Application Data

(63) Continuation of application No. 14/771,448, filed as application No. PCT/EP2014/053858 on Feb. 27, 2014, now Pat. No. 10,125,094.

(30) Foreign Application Priority Data

Feb. 28, 2013 (EP) .................................. 13157232
May 31, 2013 (EP) .................................. 13170069

(51) Int. Cl.
| | | |
|---|---|---|
| *C07C 311/37* | (2006.01) | |
| *A61K 31/18* | (2006.01) | |
| *C07C 311/16* | (2006.01) | |
| *C07C 311/17* | (2006.01) | |
| *C07C 311/18* | (2006.01) | |
| *C07C 311/19* | (2006.01) | |
| *C07C 317/28* | (2006.01) | |
| *A61K 45/06* | (2006.01) | |
| *A61K 31/27* | (2006.01) | |
| *A61K 31/277* | (2006.01) | |

(52) U.S. Cl.
CPC ............ *C07C 311/37* (2013.01); *A61K 31/18* (2013.01); *A61K 31/27* (2013.01); *A61K 31/277* (2013.01); *A61K 45/06* (2013.01); *C07C 311/16* (2013.01); *C07C 311/17* (2013.01); *C07C 311/18* (2013.01); *C07C 311/19* (2013.01); *C07C 317/28* (2013.01)

(58) Field of Classification Search
CPC ... C07C 311/37; C07C 311/16; C07C 311/17; C07C 311/18; C07C 311/19; C07C 317/28; A61K 31/27; A61K 31/277; A61K 31/18; A61K 45/06; A61P 31/00; A61P 31/20

See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |

(Continued)

FOREIGN PATENT DOCUMENTS

| | | |
|---|---|---|
| CA | 2950807 A1 | 12/2013 |
| CN | 1390201 A | 1/2003 |

(Continued)

OTHER PUBLICATIONS

Nijampatnam et al., "Recent advances in the development of HBV capsid assembly modulators", Current Opinion in Chemical Biology, vol. 50; pp. 73-79 (2019).

(Continued)

*Primary Examiner* — Barbara P Badio

(57) ABSTRACT

Inhibitors of HBV replication of Formula (I)

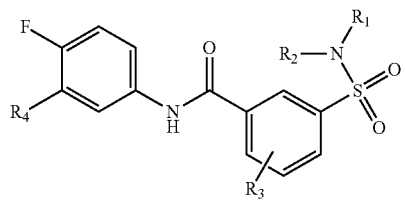

including stereochemically isomeric forms, salts, hydrates and solvates thereof, wherein $R_1$, $R_2$, $R_3$ and $R_4$ have the meaning as defined herein.

The present invention also relates to processes for preparing said compounds, pharmaceutical compositions containing them and their use, alone or in combination with other HBV inhibitors, in HBV therapy.

10 Claims, No Drawings

(56) References Cited

U.S. PATENT DOCUMENTS

| | | |
|---|---|---|
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334682 A1 | 11/2017 | Hartman et al. |

FOREIGN PATENT DOCUMENTS

| | | |
|---|---|---|
| CN | 101039919 A | 9/2007 |
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| WO | 198403281 A1 | 8/1984 |
| WO | 1992/07835 A1 | 5/1992 |

(56) References Cited

FOREIGN PATENT DOCUMENTS

| | | |
|---|---|---|
| WO | 1998023285 A1 | 6/1998 |
| WO | 1999/09022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001025200 A1 | 4/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003/002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005000231 A3 | 5/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006/053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | WO2008054605 A3 | 7/2008 |
| WO | 2008093614 A1 | 8/2008 |
| WO | 2008137794 A1 | 11/2008 |
| WO | 2008154819 A1 | 12/2008 |
| WO | 2009/018219 A2 | 2/2009 |
| WO | 2009016068 A1 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | 2013006394 A1 | 1/2013 |
| WO | 2013/096744 A1 | 6/2013 |
| WO | 2013102655 A1 | 7/2013 |
| WO | 2013130703 A2 | 9/2013 |
| WO | 2013144129 A1 | 10/2013 |
| WO | 2013/174962 | 11/2013 |
| WO | 2013181584 A2 | 12/2013 |
| WO | 2013184757 A1 | 12/2013 |
| WO | 2014/033176 | 3/2014 |
| WO | 2014033167 A1 | 3/2014 |
| WO | 2014033170 A1 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2019011323 A1 | 1/2019 |

OTHER PUBLICATIONS

Online Registry via STN Dec. 22, 2008, RN 1088200-12-7.
Online Registry via STN, Mar. 2, 2007, RN 924514-21-6.
Online Registry via STN, Sep. 2, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).
Cai, et al., "Identification of disubstituted sulfonamide compounds as specific inhibitors of hepatitis B virus covalently closed circular DNA formuation, Antimicrobial agents and chemotherapy" , pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).
Campagna, "Sulfamoylbenzamide Derivatives are a Novel Class of Hepatities B Virus inhibitors Targeting PGRNA Encapsidation", 2011 International Meeting on Molecular Biology of Hepatitis B Viruses, Poster Presentation, (Oct. 9-12, 2011).
Carver, et al., Polyfunctionalisation of Imidazole via Sequential Imidazolyl Anion Formation, Tetrahedron, 1997, pp. 14481-14496, vol. 53 Issue 42.

(56) References Cited

OTHER PUBLICATIONS

Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Chemdiv, Inc., 1H-Pyrazole-4-carboxamide, 1-ethyl-N-phenyl-3-(4-thiomorpholinylaulfonyl1)—(CA Index Name), CHEMCATS, Mar. 2, 2012, pp. 1-1, RN 1359596-55-6 Registry.
Chemdiv, Inc., 1H-PyraZole-4-carboxamide, N-(4-fluoro-3-methylphenyl)-3-{ (hexahydro-1H- azepin-1-y1) sulfonyl1]-1-methyl—(CA Index Name), CHEMCATS, Mar. 2, 2012, pp. 1-1, RN 1359583-56-4 Registry.
Cho, et al., "2-Amino-N-(2,6-dichloropyridin-3-yl)acetarnide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an uraent global public health priority demanding action", Antiviral Therapy,vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano—4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al., Synthesis of some Thiazolo-[3,2-a]Pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors"; Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).
Horig, et al., from bemnch to Clinic and back : Perspective on the 1st IQPC translational Research conference, Journal of translational medicine, Dec. 20, 2004, pp. 1-8, vol. 2 Issue 44.
Huang, et al., "Blockage of HBV Virus Replication and inhibition of cccDNA Establishment by Core Protein Allosteric Modifiers (CpAMs)", Hepatology, vol. 64 (1 Suppl): pp. 937A-938A, ( Oct. 2016).
Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinforrnatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Mohebbi, et al., An Overview of Hepatitis B Virus Surface Antigen Secreation Inhibitors, Frontier in Microbiology, Apr. 5, 2018, pp. 1-9, vol. 9.
Online Registr via STN, Dec. 28, 2008, RN 1090750-88-1.
Online Registry via STN , Aug. 13, 2012, RN 1390589-54-4.
Online Registry via STN Feb. 2, 2007, RN 919040-39-4.

(56) References Cited

OTHER PUBLICATIONS

Online Registry via STN Feb. 2, 2007, RN 919040-53-2.
Online Registry via STN Feb. 2, 2007, RN 919040-55-4.
Online Registry via STN Feb. 3, 2012, RN 1359583-56-4.
Online Registry via STN Feb. 3, 2012, RN 1359596_55_6.
Online Registry via STN Aug. 6, 2012. RN 1386725-02-5.
Online Registry via STN Jun. 7, 2012, RN 1375909-37-7.
Online Registry via STN Dec. 8, 2012, RN 1389720-57-3.
Online Registry via STN Oct. 10, 2001, RN 361373-90-2.
Online Registry via STN Dec. 11, 2007, RN 957487-45-5.
Online Registry via STN Dec. 11, 2007, RN 957487-49-9.
Online Registry via STN Aug. 12, 2012, RN 1389686-79-6.
Online Registry via STN Aug. 13, 2012, RN 1390500-09-0.
Online Registry via STN Jan. 16, 2001, RN 314043-17-9.
Online Registry via STN Mar. 17, 2013, RN 1424462-66-7.
Online Registry via STN Sep. 18, 2012, RN 1394742-82-5.
Online Registry via STN 2010, RN 1253220-91-5.
Online Registry via STN Aug. 30, 2011, RN 1325664-90-1.
Online Registry via STN, Jan. 24, 2008, RN 296790-26-6.
Online Registry via STN, Feb. 2, 2007, RN 9019040-48-5.
Online Registry via STN, Feb. 2, 2007, RN 919040-37-2.
Online Registry via STN, May 6, 2011, RN 1291044-81-9.
Online Registry via STN, Sep. 6, 2011, RN 1328738-57-3.
Online Registry via STN, Oct. 7, 2008, RN 1057788-44-9.
Online Registry via STN, Oct. 7, 2008, RN 1057871-39-2.
Online Registry via STN, Jan. 9, 2001, RN 313253-89-3.
Online Registry via STN, Mar. 10, 2010, RN 1208400-27-4.
Online Registry via STN, Feb. 15, 2007, RN 921179-95-5.
Online Registry via STN, Aug. 15, 2011, RN 1317923-24-2.
Online Registry via STN, Aug. 15, 2011, RN 1318022-74-0.
Online Registry via STN, Mar. 17, 2003, RN 499189-09-2.
Online Registry via STN, May 18, 2011, RN 1296380-95-4.
Online Registry via STN, Oct. 18, 2000, RN 296894-70-7.
Online Registry via STN, Sep. 20, 2013, RN 1452780-00-5.
Online Registry via STN, Apr. 24, 2002, RN 406926-60-1.
Online Registry via STN, Apr. 28, 2011, RN 1286906-97-5.
Online Registry via STN. Apr. 19, 2008, RN 930914-71-9.
Patani, et al., "Bioisoterisrn: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schafer, et al., Failure is option: learning from unsuccessful proof-ofconcepts trails, Drug Discovery Today, 2008, pp. 913-916, vol. 13 Issue 21/22.
Schroder, et al., "Arzneimittelchemie Passage", Arzneimittelchemei Grundlagen Nerven Musklen and Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).

Stray, et al., "Bay 41-4109 has multiple effects on Hepatitis B virus capsid assembly", Journal of Molecular Recognition,vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber, et al, "Inhibition of human hepatitis B virus (HBV) by a novel non-nucleosidic compound in a transgenic mouse model", Antiviral Research, vol. 54 (2): pp. 69-78 (Jan. 1, 2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, Nz-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Basarab et al., Design of Helicobacter pylori glutamate racemase inhibitors as selective antibacterial agents : a novel pro-drug approach to increase exposure, Bioorg. Med. Chem. Lett., vol. 18; pp. 4716-4722 (Aug. 15, 2008).

(56) References Cited

OTHER PUBLICATIONS

Moranta et al., "Synthesis and properties of 1-alkyl-2-methyl-3-sulfonylpyrroles and 1-alkyl-2-methyl-3-sulfonylpyrrole-5-carboxylic acid derivates", J. Chem. Soc. Perkin Trans., vol. 19: pp. 3285-3292 (1998).
Online Registry via STN Aug. 24, 2019, RN 1275589-30-4.
Online Registry via STN Aug. 24, 2019, RN 311800-19-8.
Online Registry via STN Aug. 24, 2019, RN 312756-74-4.
Online Registry via STN Aug. 24, 2019, RN 312756-75-5.
Online Registry via STN Aug. 24, 2019, RN 313225_30_8.
Online Registry via STN Aug. 24, 2019, RN 313254-27-2.
Online Registry via STN 10.10.1987, RN 110644-97-8.
Online Registry via STN 16.07.1992, RN 142428-99-7.
Online Registry via STN 18.03.2010, RN 1211415-65-4.

SULFAMOYL-ARYLAMIDES AND THE USE THEREOF AS MEDICAMENTS FOR THE TREATMENT OF HEPATITIS B

CROSS-REFERENCE TO RELATED APPLICATIONS

This application is a continuation of U.S. patent application Ser. No. 14/771,448, filed on Aug. 28, 2015, which is a national phase entry of International Application No. PCT/EP2014/053858, filed on Feb. 27, 2014, which claims priority to EP Patent Application No. 13157232.3, filed on Feb. 28, 2013 and EP Patent Application No. 13170069.2 filed on May 31, 2013, each of which is incorporated herein in its entirety.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO/2013/006394, published on Jan. 10, 2013, relates to a subclass of Sulphamoyl-arylamides active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to compounds of Formula (I):

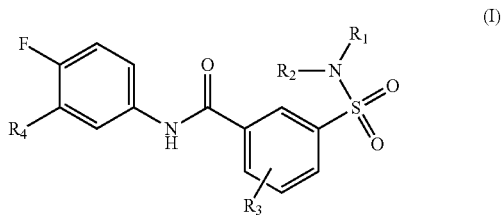

or a stereoisomer or tautomeric form thereof, wherein:
$R_1$ represents hydrogen;
$R_2$ represents $C_1$-$C_8$alkyl substituted with one or more $R_5$,
$R_3$ represents Hydrogen or methyl;
$R_4$ represents methyl;
Each $R_5$ is independently selected from the group consisting of —C≡CH, —CN, —OH, oxo, $C_1$-$C_4$alkyloxy, —C(=O)O—$R_6$, —C(=O)N($R_6$)$_2$, —N($R_6$)$_2$, —NR$_9$C(=O)—$R_6$, —NR$_9$C(=O)O—$R_6$ and SO$_2$R$_9$;
Each $R_6$ independently represents hydrogen or $C_1$-$C_3$alkyl;
$R_9$ represents hydrogen or $C_1$-$C_3$alkyl;
or a pharmaceutically acceptable salt or a solvate thereof.

The invention further relates to a pharmaceutical composition comprising a compound of Formula (I), and a pharmaceutically acceptable carrier.

The invention also relates to the compounds of Formula (I) for use as a medicament, preferably for use in the prevention or treatment of an HBV infection in a mammal.

In a further aspect, the invention relates to a combination of a compound of Formula (I), and another HBV inhibitor.

Definitions

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like $C_{1-8}$alkyl as a group or part of a group defines straight or branched chain saturated hydrocarbon radicals having from 1 to 8 carbon atoms such as the groups defined for $C_{1-6}$alkyl and heptyl, octyl, and their branched structural isomers.

The term "$C_{1-3}$alkyloxy" as a group or part of a group refers to a radical having the Formula —OR$^c$ wherein R$^c$ is $C_{1-3}$alkyl. Non-limiting examples of suitable $C_{1-3}$alkyloxy include methyloxy (also methoxy), ethyloxy (also ethoxy), propyloxy and isopropyloxy.

The term oxo, C(=O), or carbonyl refers to a group composed of a carbon atom double bonded to an oxygen atom.

The term halo and halogen are generic to fluoro, chloro, bromo or iodo. Preferred halogens are fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

For therapeutic use, the salts of the compounds of Formula (I) are those wherein the counter ion is pharmaceutically or physiologically acceptable. However, salts having a pharmaceutically unacceptable counter ion may also find use, for example, in the preparation or purification of a pharmaceutically acceptable compound of Formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural Formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of Formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

DETAILED DESCRIPTION OF THE INVENTION

Whenever used hereinafter, the term "compounds of Formula (I)", or "the present compounds" or similar term is meant to include the compounds of general Formula (I) (Ib), salts, stereoisomeric forms and racemic mixtures or any subgroups thereof.

The present invention relates to compounds of Formula (I)

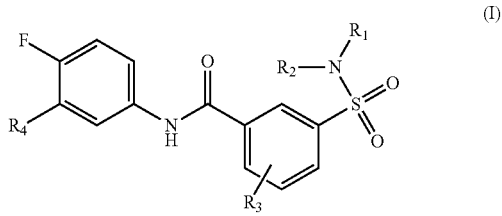

or a stereoisomer or tautomeric form thereof, wherein:
$R_1$ represents hydrogen;
$R_2$ represents $C_1$-$C_8$alkyl substituted with one or more $R_5$,
$R_3$ represents Hydrogen or methyl;
$R_4$ represents methyl;
Each $R_5$ is independently selected from the group consisting of —C≡CH, —CN, —OH, oxo, $C_1$-$C_4$alkyloxy, —C(=O)O—$R_6$, —C(=O)N($R_6$)$_2$, —N($R_6$)$_2$, —NR$_9$C(=O)—$R_6$, —NR$_9$C(=O)O—$R_6$ and SO$_2$R$_9$;
Each $R_6$ independently represents hydrogen or $C_1$-$C_3$alkyl;
$R_9$ represents hydrogen or $C_1$-$C_3$alkyl;

or a pharmaceutically acceptable salt or a solvate thereof.

In one embodiment, compounds of Formula (I) are provided wherein:
$R_1$ represents hydrogen;
$R_2$ represents $C_1$-$C_8$alkyl substituted with one or more $R_5$,
$R_3$ represents Hydrogen or methyl;
$R_4$ represents methyl;
$R_5$ is selected from the group consisting of —C≡CH, —CN, —OH, oxo, $C_1$-$C_4$alkyloxy, —C(=O)O—$R_6$, —C(=O)N($R_6$)$_2$, —N($R_6$)$_2$, —N$R_9$C(=O)—$R_6$, —N$R_9$C(=O)O—$R_6$ and $SO_2R_7$;
$R_6$ represents hydrogen or $C_1$-$C_3$alkyl;
$R_9$ represents hydrogen or $C_1$-$C_3$alkyl;
or a pharmaceutically acceptable salt or a solvate thereof.

In a further embodiment, compounds of Formula (I) are provided wherein:
$R_1$ represents hydrogen;
$R_2$ represents $C_1$-$C_6$alkyl substituted with one $R_5$,
$R_3$ represents Hydrogen;
$R_4$ represents methyl;
$R_5$ is selected from the group consisting of —C≡CH, —CN, —OH, $C_1$-$C_4$alkyloxy, —C(=O)O—$R_6$, —C(=O)N($R_6$)$_2$, —N($R_6$)$_2$, —NHC(=O)—$R_6$ and —NHC(=O)O—$R_6$;
$R_6$ represents hydrogen or $C_1$-$C_3$alkyl;
or a pharmaceutically acceptable salts or a solvate thereof.

In another embodiment, compounds of Formula (I) are provided wherein the $C_1$-$C_8$alkyl group as defined in $R_2$ represents a branched $C_2$-$C_6$alkyl.

In yet another embodiment, at least one $R_5$ is —OH.

In a subembodiment, such compounds are represented by Formula (Ib):

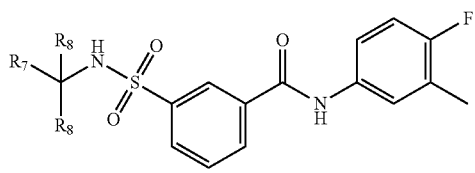

(Ib)

wherein:
$R_7$ is selected from the group consisting of —C≡CH, —CN, —C(=O)O—$R_6$—C(=O)N($R_6$)$_2$ and $C_1$-$C_4$alkyl optionally substituted with one or more substituents selected from the group consisting of —C≡CH, —CN, —OH, oxo, $C_1$-$C_4$alkyloxy, —C(=O)O—$R_6$, —C(=O)N($R_6$)$_2$, —N($R_6$)$_2$, —N$R_9$C(=O)—$R_6$, —N$R_9$C(=O)O—$R_6$ and $SO_2R_9$;
$R_6$ represents hydrogen or $C_1$-$C_3$alkyl;
$R_9$ represents hydrogen or $C_1$-$C_3$alkyl and wherein
Each $R_8$ independently represents hydrogen or $C_1$-$C_2$alkyl optionally substituted with OH.

In a sub-embodiment, compounds are according to Formula (Ib) are provided wherein $R_7$ is selected from the group consisting of —C≡CH, —CN, —C(=O)O—$R_6$—C(=O)N($R_6$)$_2$ and $C_1$-$C_4$alkyl optionally substituted with one or more substituents selected from the group consisting of —C≡CH, —CN, —OH, $C_1$-$C_4$alkyloxy, —C(=O)O—$R_6$, —C(=O)N($R_6$)$_2$, —N($R_6$)$_2$, —NHC(=O)—$R_6$ and —NHC(=O)O—$R_6$;
$R_6$ represents hydrogen or $C_1$-$C_3$alkyl; and wherein
Each $R_8$ independently represents hydrogen or $C_1$-$C_2$alkyl optionally substituted with OH. In one aspect, one $R_8$ is $C_1$-$C_2$alkyl substituted with OH.

In another subembodiment, compounds according to Formula (Ib) are provided wherein $R_7$ is selected from the group consisting of $C_1$-$C_4$alkyl optionally substituted with —C≡CH, —CN, —OH, $C_1$-$C_4$alkyloxy, —C(=O)O—$R_6$, —C(=O)N($R_6$)$_2$, —N($R_6$)$_2$, —NHC(=O)—$R_6$ and —NHC(=O)O—$R_6$.

Further combinations of any of the sub- or preferred embodiments are also envisioned to be in the scope of the present invention.

Preferred compounds according to the invention are compound or a stereoisomer or tautomeric form thereof with a Formula selected from table 1.

In a further aspect, the present invention concerns a pharmaceutical composition comprising a therapeutically or prophylactically effective amount of a compound of Formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (I).

The compounds of Formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection. In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (I) or any subgroup thereof, as specified herein with other anti-HBV agents. The term "combination" may relate to a product or kit containing (a) a compound of Formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of Formula (I) or any subgroup thereof with at least one anti-HBV agent. In a particular embodiment, the invention concerns combination of a compound of Formula (I) or any subgroup thereof with at least two anti-HBV agents. In a particular embodiment, the invention concerns combination of a compound of Formula (I) or any subgroup thereof with at least three anti-HBV agents. In a particular embodiment, the invention concerns combination of a compound of Formula (I) or any subgroup thereof with at least four anti-HBV agents.

The combination of previously known anti-HBV agents, such as interferon-α (IFN-α), pegylated interferon-α, 3TC, adefovir or a combination thereof, and, a compound of Formula (I) or any subgroup thereof can be used as a medicine in a combination therapy.

Generic Synthesis:

The substituent represented by $R_2$ in this general synthesis section are meant to include any substituent or reactive species that is suitable for transformation into any $R_2$ substituent according to the present invention without undue burden for the person skilled in the art.

A possible synthesis of compound of general Formula (I) is described in scheme 1 and 2.

A carboxylic acid chloride of general Formula II can be selectively reacted with an aniline of general Formula III, for example in an organic solvent like $CH_2Cl_2$ in the presence of an organic base like triethylamine or DIPEA (N,N-diisopropylethylamine), or, as another example, by addition of the aniline III to a refluxing toluene solution of compound II, resulting in compound IV. The remaining sulfonic acid chloride functionality in compound IV is further reacted with an amine of general Formula V, resulting in a compound of general Formula (I). Alternatively a compound of general Formula (I) might be obtained as described in scheme 2. This time the sulfonic acid chloride VI is reacted with an amine of general Formula V, for example in an organic solvent like $CH_2Cl_2$ in the presence of an organic base like triethylamine or DIPEA or, as another example, in the presence of $Na_2CO_3$ in a mixture of $H_2O$/THF. The resulting compound VII is coupled with aniline of general Formula III in the presence of an activating reagent like for example HATU and an organic base like triethylamine or DIPEA.

Scheme 1

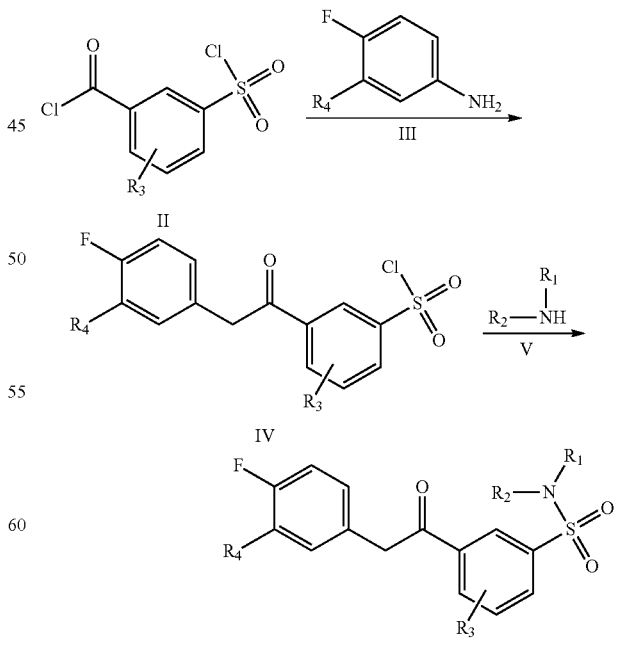

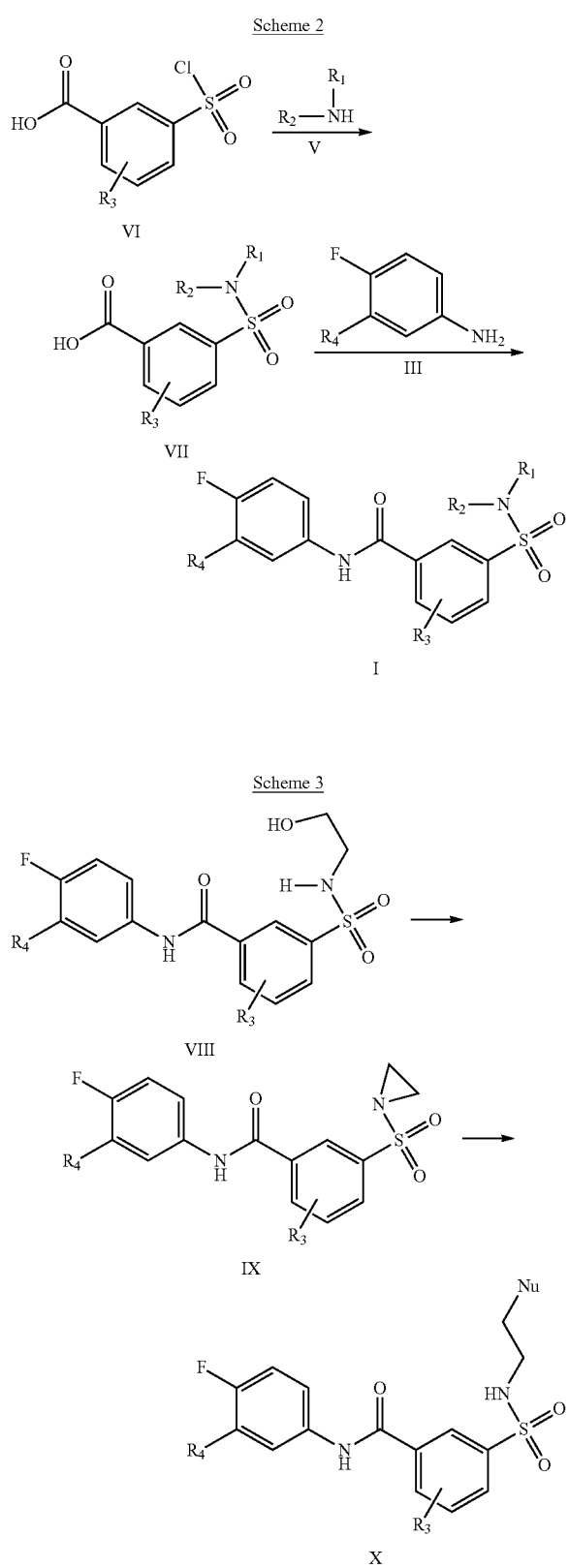

Scheme 2

Scheme 3

A synthetic route to compounds of general Formula X is described in Scheme 3. A aminoethanol derivative VIII, prepared as described in scheme 1 for the compounds of general Formula (I), is transformed in an aziridine derivative IX by treatment with Diethyl diazene-1,2-dicarboxylate and PPh$_3$ in THF. The aziridine of general Formula IX is reacted with a nucleophile Nu, resulting in a compound of general Formula X. Examples of such nucleophiles (Nu) are, but are not limited to, ammonia, methanamine and dimethylamine. In case ammonia is used, the resulting primary amine can be reacted with for example acetyl chloride, or methyl chloroformate, like for example used in the synthesis of compounds 1 and 9. Examples of a compounds synthesized according to the route described in scheme 3, are compounds 2 and 3.

Synthesis of Compounds:

LC-MS Methods:

Method A: mobile phase A: H$_2$O (0.1% TFA; B:CH$_3$CN (0.05% TFA) Stop Time: 10 min; gradient time(min) [% A/% B] 0.0 [100/0] to 1 [100/0] to 5 [40/60] to 7.5 [40/60] to 8.0 [100/0]; flow: 0.8 mL/min; column temp.: 50° C., YMC-PACK ODS-AQ, 50×2.0 mm 5 µm Method B: mobile phase A: H$_2$O (0.1% TFA; B:CH$_3$CN (0.05% TFA) Stop Time: 10 min; gradient time(min) [% A/% B] 0.0 [90/10] to 0.8 [90/10] to 4.5 [20/80] to 7.5 [20/80] to 8.0 [90/10]; flow: 0.8 mL/min; column temp.: 50° C., YMC-PACK ODS-AQ, 50×2.0 mm 5 µm Method C: mobile phase A: H$_2$O (0.1% TFA); B:CH$_3$CN (0.05% TFA) Stop Time: 10 min; gradient time(min) [% A/% B] 0.0 [90/10] to 0.8 [90/10] to 4.5 [20/80] to 7.5 [20/80]; 9.5 [90/10] flow: 0.8 mL/min; column temp.: 50° C.; Agilent TC-C18, 50×2.1 mm, 5 µm Method D: mobile phase A: H$_2$O (0.05% NH$_3$.H$_2$O); B: CH$_3$CN Stop Time: 10 min; gradient time(min) [% A/% B] 0.0 [100/0] to 1 [100/0] to 5 [40/60] to 7.5 [40/60]; 8 [100/0] flow: 0.8 mL/min; column temp.: 40° C., XBridge Shield-RP18, 50*2.1 mm 5 µm Method E: mobile phase A: H$_2$O (0.1% TFA; B:CH$_3$CN (0.05% TFA) Stop Time: 10 min; Post Time: 0.5 min; gradient time(min) [% A/% B]0 [100/0] to 1 [100/0] to 5 [40/60] to 7.5 [15/85] to 9.5 [100/0]; flow: 0.8 mL/min; column temp.: 50° C., Agilent TC-C18, 50×2.1 mm, 5 µm Method F: The LC measurement was performed using an Acquity UPLC (Waters) system with column heater (set at 55° C.). Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 mL/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode and 20 V for negative ionization mode.

Method G: The LC measurement was performed using an Acquity UPLC (Waters) with column heater (set at 55° C.). Reversed phase UPLC (Ultra Performance Liquid Chromatography) was carried out on a Acquity UPLC HSS T3 column (1.8 m, 2.1×100 mm; Waters Acquity) with a flow rate of 0.8 mL/min. Two mobile phases (A: 10 mM ammonium acetate in H$_2$O/acetonitrile 95/5; mobile phase B: acetonitrile) were used to run a gradient condition from 100% A and 0% B to 5% A and 95% B in 2.1 minutes and subsequently to 0% A and 100% B in 0.9 minutes to 5% A and 95% B in 0.5 min. An injection volume of 1 µl was used. Cone voltage was 30 V for positive ionization mode and 30 V for negative ionization mode.

Procedure S1:

A solution of 3-[(4-fluoro-3-methyl-phenyl)carbamoyl] benzenesulfonyl chloride (0.50 g, 1.52 mmol, 1 eq) in toluene (10 mL) was added to a flask containing an amine (1.1 eq). DIPEA (657 µL, 3.81 mmol, 2.5 eq) was added and the reaction mixture was stirred for 1 hour. Next, 1M HCl (5 mL) was added to the reaction mixture.

Procedure S2:

A tube was charged with 3-[(4-fluoro-3-methyl-phenyl)carbamoyl]-benzenesulfonyl chloride (250 mg, 0.76 mmol) and an amine (1.1 eq) and CH$_2$Cl$_2$ (5 mL) was added. The solution was stirred, DIPEA (329 µL, 1.9 mmol, 2.5 eq) was added and the mixture was further stirred for 30 minutes. Then, HCl (1M aq/5 mL) was added and the mixture was stirred for 5 minutes more.

Procedure S3:

To a solution of 3-[(4-fluoro-3-methyl-phenyl)carbamoyl] benzenesulfonyl chloride (0.50 g, 1.52 mmol, 1 eq) and DIPEA (657 µL, 3.81 mmol, 2.5 eq) in CH$_2$Cl$_2$ (10 mL), an amine (1.1 eq) was added. The reaction mixture was stirred for 1 hour. Next, 1M HCl (5 mL) was added to the reaction mixture.

Procedure S4:

3-[(4-fluoro-3-methyl-phenyl)carbamoyl]benzenesulfonyl chloride (250 mg, 0.76 mmol) and DIPEA (329 µL, 1.9 mmol, 2.5 eq) dissolved in CH$_2$Cl$_2$ (5 mL) were added to a tube containing an amine (1.1 eq). The reaction mixture was stirred for 3 hours. 1M HCl (5 mL) was added.

Workup W1:

A precipitate was formed. The precipitate was filtered off, rinsed with diisopropylether and dried in a vacuum oven at 55° C.

Workup W2:

The organic layer was separated and concentrated in vacuo. The obtained residue was purified by silica gel column chromatography using a heptane to EtOAc gradient as eluent.

Workup W3:

The layers were separated and the organic layer was loaded on a silica gel column for purification (with gradient elution: CH$_2$Cl$_2$-methanol 100:0 to 97:3).

Workup W4:

The organic layer was separated and loaded on a silica gel column. The mixture was purified using gradient elution from heptane to EtOAc.

Compound 1

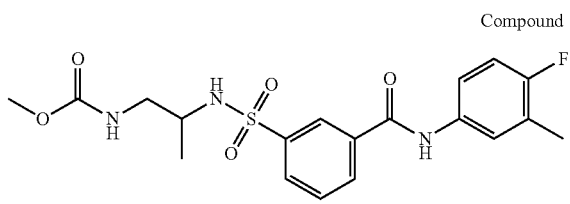

4-fluoro-3-methyl-aniline (9.04 g, 72.2 mmol) was added drop wise to a solution of 3-(chlorosulfonyl) benzoyl chloride (19.0 g, 79.47 mmol) in toluene (300 mL) at 110° C. The resultant mixture was stirred at 110° C. for 1 hour and allowed to cool to 20° C. over night. The precipitate was filtered and recrystallized from dry toluene resulting in 3-[(4-fluoro-3-methyl-phenyl)carbamoyl]benzenesulfonyl chloride (20 g). 3-[(4-fluoro-3-methyl-phenyl)carbamoyl] benzenesulfonyl chloride (15 g, 45.77 mmol) was added drop wise at 0° C. to a solution of 2-aminopropan-1-ol (3.437 g, 45.77 mmol) and triethylamine (6.946 g) in THF (200 mL). The resultant mixture was stirred for 10 minutes and then allowed to warm to 20° C. during 2 hours. The reaction mixture was quenched with 1N HCl (50 mL). The mixture was extracted with dichloromethane (3×30 mL). The combined organic layers were washed with brine, dried over MgSO$_4$, filtered and concentrated in vacuo. The residue was purified by silica gel column chromatography (gradient eluent: petroleum ether/ethyl acetate from 100/1 to 50/50), resulting in N-(4-fluoro-3-methyl-phenyl)-3-[(2-hydroxy-1-methyl-ethyl)sulfamoyl]-benzamide (15.6 g). Diethyl diazene-1,2-dicarboxylate (4.91 g, 28.19 mmol) was added drop wise to a solution of N-(4-fluoro-3-methyl-phenyl)-3-[(2-hydroxy-1-methyl-ethyl)sulfamoyl]benzamide (7.8 g, 21.29 mmol) and PPh$_3$ (6.14 g, 23.41 mmol) in THF (500 mL) at −70° C. under Argon. The resultant mixture was stirred for 1 hour and then allowed to warm to 20° C. over night. The reaction mixture was quenched with 1N HCl (300 mL). The mixture was extracted with dichloromethane (4×400 mL) and the combined organic layers were washed with brine, dried over MgSO$_4$, filtered and concentrated in vacuo. The obtained residue was purified by silica gel column chromatography (gradient eluent: petroleum ether/ethyl acetate from 100/1 to 60/40) resulting in N-(4-fluoro-3-methyl-phenyl)-3-(2-methylaziridin-1-yl)sulfonyl-benzamide (6.5 g). To N-(4-fluoro-3-methyl-phenyl)-3-(2-methylaziridin-1-yl)sulfonyl-benzamide (200 mg, 0.574 mmol), NH$_3$ (NH$_3$ in methanol, 8 mL) was added drop wise at 0° C. The mixture was stirred at 20° C. over night. The solvent was removed and the obtained residue (170 mg) containing 3-[(2-amino-1-methyl-ethyl)sulfamoyl]-N-(4-fluoro-3-methyl-phenyl) benzamide used as such in the next step. 3-[(2-amino-1-methyl-ethyl)sulfamoyl]-N-(4-fluoro-3-methyl-phenyl) benzamide (0.17 g, 0.465 mmol) and triethylamine (94 mg) were dissolved in anhydrous CH$_2$Cl$_2$ (20 mL) and methyl chloroformate (0.5 g, 5.29 mmol) was added drop wise at 0° C. 1 N HCl (10 mL) was added, the organic layer was separated and the aqueous layer was extracted with dichloromethane (20 mL). The combined organic layers were washed with brine and dried over Na$_2$SO$_4$. The solvent was removed in vacuo and the obtained residue was purified by reversed phase high performance liquid chromatography (eluent: CH$_3$CN in water (0.5% NH$_3$H$_2$O) from 35% to 65%, v/v). The relevant fractions were concentrated in vacuo and the residual aqueous fraction lyophilized to dryness resulting in compound 1 (70 mg). Method A; Rt: 5.14 min. m/z: 424.3 (M+H)$^+$ Exact mass: 423.1. $^1$H NMR (400 MHz, DMSO-d$_6$) δ ppm 0.85 (d, J=6.5 Hz, 3H) 2.24 (s, 3H) 2.80-2.99 (m, 2H) 3.16-3.32 (m, 1H) 3.44 (s, 3H) 7.05 (t, J=5.8 Hz, 1H) 7.14 (t, J=9.2 Hz, 1H) 7.51-7.63 (m, 1H) 7.63-7.71 (m, 1H) 7.71-7.83 (m, 2H) 7.99 (d, J=7.8 Hz, 1H) 8.20 (d, J=7.8 Hz, 1H) 8.36 (s, 1H) 10.47 (s, 1H).

Compound 2

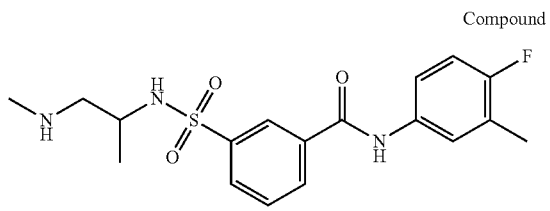

N-(4-fluoro-3-methyl-phenyl)-3-(2-methylaziridin-1-yl) sulfonyl-benzamide (0.30 g, 0.861 mmol), methanamine (0.134 g, 4.305 mmol) and triethylamine (0.523 g) were dissolved in anhydrous 1,4-dioxane (8 mL). This mixture was stirred at 150° C. in an autoclave under argon for 30 minutes. The volatiles were removed in vacuo and the obtained residue was purified by reversed phase high performance liquid chromatography (eluent: CH₃CN in water (0.075% TFA) from 15% to 45%, v/v). The pure fractions were collected and adjusted to pH=7 with Amberlite IRA-900 OH-anionic exchange resin. The resin was filtered off, the filtrate was concentrated in vacuo and the residual aqueous layer lyophilized to dryness, resulting in compound 2 (130 mg). Method A; Rt: 4.27 min. m/z: 380.3 (M+H)⁺ Exact mass: 379.1.

Compound 3

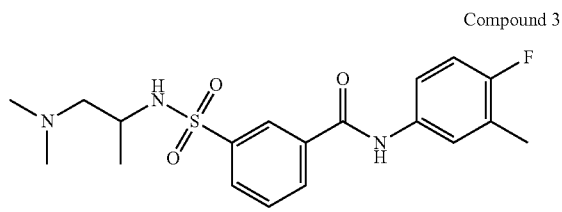

N-(4-fluoro-3-methyl-phenyl)-3-(2-methylaziridin-1-yl) sulfonyl-benzamide (0.35 g, 1.0 mmol), dimethylamine hydrochloride (0.41 g, 5.025 mmol) and triethylamine (0.61 g) were dissolved in anhydrous 1,4-dioxane (8 mL). This mixture was stirred at 150° C. in an autoclave under argon for 30 min. The solvent was removed in vacuo and the obtained residue was purified by reversed phase high performance liquid chromatography r (eluent: CH₃CN in water (0.075% TFA) from 20% to 45%, v/v). The pure fractions were collected and adjusted to pH=7 with Amberlite IRA-900 (OH) anionic exchange resin. The resin was filtered off, the filtrate was concentrated in vacuo and the residual aqueous lyophilized to dryness, resulting in compound 3. Method A; Rt: 4.40 min. m/z: 394.3 (M+H)⁺ Exact mass: 393.2.

Compound 4

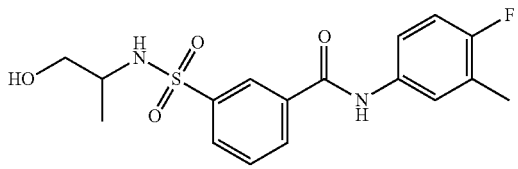

A mixture of 2-aminopropan-1-ol (229 mg, 3.05 mmol) and DIPEA (1.063 mL, 6.10 mmol) were dissolved in CH₂Cl₂ (10 mL). 3-[(4-fluoro-3-methyl-phenyl)-carbamoyl] benzenesulfonyl chloride (1 g, 3.051 mmol) was added portionwise at 0° C. and the mixture was stirred at 0° C. for 1 hour. The mixture was washed with saturated citric acid (10 mL), saturated aqueous NaHCO₃ (10 mL), brine and dried over Na₂SO₄. The solvent was removed in vacuo and the obtained residue was washed with tert-butyl methyl ether (2×5 mL). The solid was suspended in water (10 mL) and acetonitrile (10 mL) and the solution was lyophilized to dryness resulting in compound 4 (780 mg). Method A; Rt: 4.90 min. m/z: 367.3 (M+H)⁺ Exact mass: 366.1. ¹H NMR (400 MHz, DMSO-d₆) δ ppm 0.90 (d, J=6.3 Hz, 3H) 2.26 (d, J=1.5 Hz, 3H) 3.07-3.20 (m, 2H) 3.25-3.32 (m, 1H) 4.72 (t, J=5.5 Hz, 1H) 7.15 (t, J=9.3 Hz, 1H) 7.54-7.64 (m, 1H) 7.64-7.72 (m, 2H) 7.76 (t, J=7.9 Hz, 1H) 8.02 (d, J=7.8 Hz, 1H) 8.19 (d, J=7.8 Hz, 1H) 8.37 (s, 1H) 10.48 (s, 1H)

Compound 4a

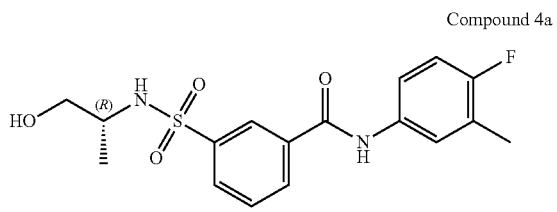

Synthesis following procedure S4 (20 hours instead of 3 hours reaction time) with D-alaninol as amine, workup W4. DSC (From 30 to 300° C. at 10° C./min): peak: 152° C. Method F; Rt: 0.83 min. m/z: 384.2 (M+NH₄)⁺ Exact mass: 366.1.

Compound 4b

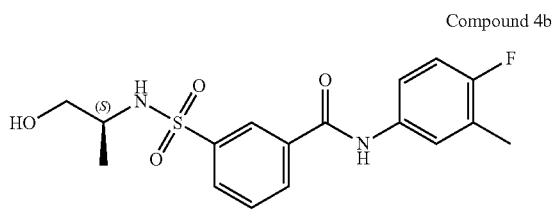

Synthesis following procedure S4 (20 hours instead of 3 hours reaction time) with L-alaninol as amine, workup W4. DSC (From 30 to 300° C. at 10° C./min): peak: 152° C. Method F; Rt: 0.83 min. m/z: 384.1 (M+NH₄)⁺ Exact mass: 366.1.

Compound 5

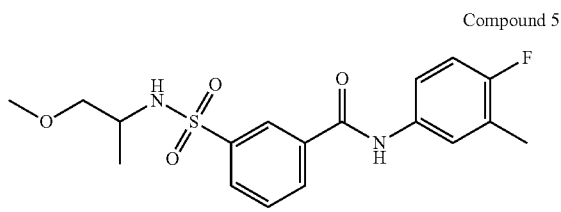 [SMILES: COCC(C)NS(=O)(=O)c1cccc(C(=O)Nc2ccc(F)c(C)c2)c1]

To a solution of 3-[(4-fluoro-3-methyl-phenyl)carbamoyl] benzenesulfonyl chloride (0.20 g, 0.60 mmol) in CH₂Cl₂ (2 mL), DIPEA (0.16 g, 1.21 mmol) was added, followed by 1-methoxypropan-2-amine (0.05 g, 0.60 mmol). After stirring at 15° C. for 1 hour, the resulting mixture was diluted with water (10 mL). The organic layer was separated, washed with 1N HCl (5 mL), aqueous NaHCO₃ (5 mL), brine (5 mL) and dried over anhydrous MgSO₄. The solvent was removed in vacuo, resulting in compound 5 (123 mg). Method A; Rt: 5.38 min. m/z: 381.3 (M+H)⁺ Exact mass: 380.1. ¹H NMR (400 MHz, DMSO-d₆) δ ppm 0.89 (d, J=6.8 Hz, 3H) 2.23 (s, 3H) 3.04-3.12 (m, 4H) 3.16 (dd, J=9.5, 5.8 Hz, 1H) 3.30-3.37 (m, 1H) 7.13 (t, J=9.2 Hz, 1H) 7.52-7.62 (m, 1H) 7.61-7.70 (m, 1H) 7.73 (t, J=7.9 Hz, 1H) 7.83 (d, J=6.5 Hz, 1H) 7.99 (d, J=7.8 Hz, 1H) 8.17 (d, J=7.8 Hz, 1H) 8.35 (s, 1H) 10.46 (s, 1H)

Compound 6

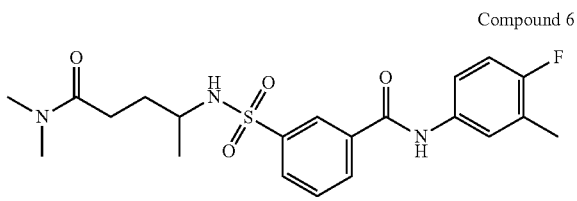 [SMILES: Cc1cc(NC(=O)c2cccc(S(=O)(=O)NC(C)CCC(=O)N(C)C)c2)ccc1F]

To a solution of 4-(tert-butoxycarbonylamino)pentanoic acid (2.17 g, 9.99 mmol), N-methylmethanamine hydrochloride (0.82 g, 10.00 mmol), EDC (2.33 g, 15.01 mmol), and HOBt (0.68 g, 5.00 mmol) in $CH_2Cl_2$ (30 mL), DIPEA (3.88 g, 30.02 mmol) was added. The resulting mixture was stirred at 15° C. for 2 hours. The resulting mixture was diluted with water (40 mL), the organic layer was separated, washed with 1 N HCl (10 mL), aqueous $NaHCO_3$ (20 mL), brine (20 mL) and dried over anhydrous $MgSO_4$. The solvent was removed in vacuo resulting in tert-butyl N-[4-(dimethylamino)-1-methyl-4-oxo-butyl]carbamate (1.00 g). To a solution of tert-butyl N-[4-(dimethylamino)-1-methyl-4-oxo-butyl]carbamate (1.00 g, 4.09 mmol) in $CH_2Cl_2$ (30 mL), TFA (30 mL) was added. The resulting mixture was stirred for 2 hours at 15° C. The reaction mixture was concentrated and the obtained residue, containing the TFA salt of 4-amino-N,N-dimethyl-pentanamide, was used directly in the next step. To a solution of the TFA salt of 4-amino-N,N-dimethyl-pentanamide (0.77 g) and 3-[(4-fluoro-3-methyl-phenyl)carbamoyl]benzenesulfonyl chloride (0.98 g, 2.99 mmol) in $CH_2Cl_2$ (15 mL) DIPEA (1.16 g, 9.00 mmol) was added at 0° C. The resulting mixture was stirred at 150 for 1 hour. The resulting mixture was washed with 1 N HCl (15 mL), aqueous $NaHCO_3$ (15 mL), brine (15 mL) and dried over anhydrous $MgSO_4$. The residue was purified by silica gel column chromatography (gradient eluent: EtOAc/petroleum ether from 0/100 to 100/0). The product fractions were collected and the solvent was evaporated resulting in compound 6 (0.62 g). Method A; Rt: 5.18 min. m/z: 436.3 $(M+H)^+$ Exact mass: 435.2. $^1H$ NMR (400 MHz, DMSO-$d_6$) δ ppm 0.94 (d, J=6.5 Hz, 3H) 1.40-1.59 (m, 2H) 2.00-2.16 (m, 2H) 2.25 (s, 3H) 2.73 (s, 3H) 2.78 (s, 3H) 3.15-3.28 (m, 1H) 7.15 (t, J=9.2 Hz, 1H) 7.55-7.64 (m, 1H) 7.65-7.84 (m, 3H) 7.99 (d, J=7.8 Hz, 1H) 8.20 (d, J=7.8 Hz, 1H) 8.36 (s, 1H) 10.49 (s, 1H)

Compound 7

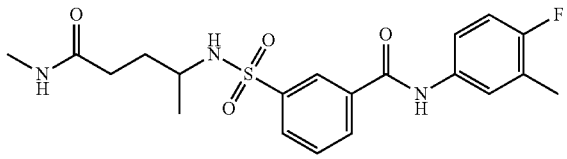

To a solution of 4-(tert-butoxycarbonylamino)pentanoic acid (1.08 g, 4.97 mmol), methanamine hydrochloride (0.68 g, 10.00 mmol), EDC (1.16 g, 7.47 mmol), and HOBt (0.34 g, 2.50 mmol) in $CH_2Cl_2$ (20 mL), DIPEA (1.94 g, 15.01 mmol) was added. The resulting mixture was stirred at 15° C. for 2 hours and then diluted with water (40 mL). The organic layer was separated, washed with 1N HCl (10 mL), aqueous $NaHCO_3$ (20 mL) and brine (20 mL) and dried over anhydrous $MgSO_4$. The solvent was removed in vacuo resulting in tert-butyl N-[1-methyl-4-(methylamino)-4-oxo-butyl]carbamate (1.00 g). To a solution of tert-butyl N-[1-methyl-4-(methylamino)-4-oxo-butyl]carbamate (0.50 g, 2.17 mmol) in $CH_2Cl_2$ (20 mL), TFA (20 mL) was added. The resulting mixture was stirred for 2 hours at 15° C. The reaction mixture was concentrated and the obtained residue was used directly in the next step. To a solution of the above obtained residue and 3-[(4-fluoro-3-methyl-phenyl)carbamoyl]-benzenesulfonyl chloride (0.718 g, 2.71 mmol) in $CH_2Cl_2$ (12 mL) DIPEA (0.84 g, 6.51 mmol) was added at 0° C. The resulting mixture was stirred at 15° C. for 1 hour and then washed with 1N HCl (15 mL), aqueous $NaHCO_3$ (15 mL), brine (15 mL) and dried over anhydrous $MgSO_4$. After removal of the solvent in vacuo, the obtained residue was purified by silica gel column chromatography (gradient eluent: EtOAc/petroleum ether from 0/100 to 100/0). The product fractions were collected and the solvent was removed in vacuo, resulting in compound 7 (0.33 g). Method A; Rt: 4.98 min. m/z: 422.3 $(M+H)^+$ Exact mass: 421.2.

Compound 8

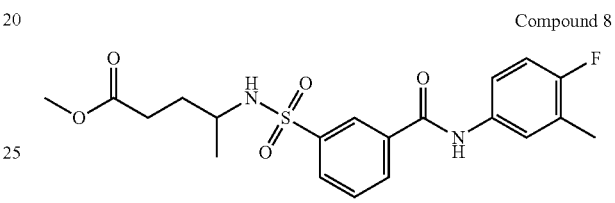

To a solution of methyl 4-aminopentanoate (0.17 g, 1.00 mmol) and 3-[(4-fluoro-3-methyl-phenyl)carbamoyl]benzenesulfonyl chloride (0.33 g, 1.00 mmol) in $CH_2Cl_2$ (8 mL), DIPEA (0.26 g, 2.02 mmol) was added at 0° C. The resulting mixture was stirred at 15° C. for 1 hour. The resulting mixture was washed with 1 N HCl (5 mL), aqueous $NaHCO_3$ (5 mL), brine (5 mL), dried over anhydrous $MgSO_4$ and the volatiles were removed in vacuo. The obtained residue was purified by silica gel column chromatography (gradient eluent: EtOAc/petroleum ether from 0/100 to 58/42). The product fractions were collected and the solvent was removed in vacuo, resulting in compound 8 (0.18 g). Method B; Rt: 4.24 min. m/z: 423.3 $(M+H)^+$ Exact mass: 422.1. $^1H$ NMR (400 MHz, DMSO-$d_6$) δ ppm 0.88 (d, J=6.8 Hz, 3H) 1.46-1.66 (m, 2H) 2.12-2.34 (m, 5H) 3.14-3.29 (m, 1H) 3.53 (s, 3H) 7.15 (t, J=9.3 Hz, 1H) 7.56-7.64 (m, 1H) 7.66-7.72 (m, 1H) 7.72-7.82 (m, 2H) 7.99 (d, J=8.0 Hz, 1H) 8.21 (d, J=8.0 Hz, 1H) 8.36 (t, J=1.5 Hz, 1H) 10.48 (s, 1H)

Compound 9

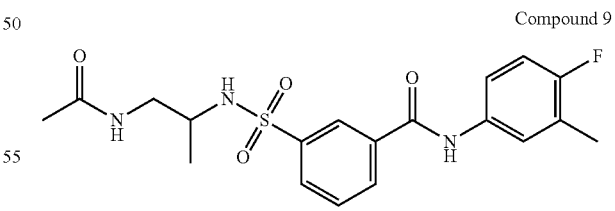

N-(4-fluoro-3-methyl-phenyl)-3-(2-methylaziridin-1-yl) sulfonyl-benzamide (3 g, 19.1 mmol) was dissolved in $NH_3$/MeOH (4 mL). The mixture was stirred for 8 hours at 0° C. The solvent was removed in vacuo an the obtained residue containing 3-[(2-amino-1-methyl-ethyl)sulfamoyl]-N-(4-fluoro-3-methyl-phenyl)benzamide was used in the next step without further purification. 3-[(2-amino-1-methyl-ethyl)-sulfamoyl]-N-(4-fluoro-3-methyl-phenyl) benzamide (200 mg, 0.491 mmol) and acetyl chloride (77.3 mg, 0.985 mmol) was dissolved in dichloromethane (3 mL). DIPEA (212 mg, 1.64 mmol) was added drop wise at 0° C. The mixture was stirred for 8 hours at 25° C. The mixture was washed with saturated citric acid (10 mL), saturated aqueous NaHCO$_3$ (10 mL) and brine and dried over Na$_2$SO$_4$. The solvent was removed in vacuo and the obtained crude was purified by preparative high-performance liquid chromatography (column: Luna 150*30 mm*5 u, mobile phase: CH$_3$CN in water (0.5% NH$_4$HCO$_3$) from 36% to 66%). The pure fractions were collected and the volatiles were removed in vacuo resulting in compound 9 (200 mg). Method A; Rt: 4.92 min. m/z: 408.3 (M+H)$^+$ Exact mass: 407.1.

Compound 10

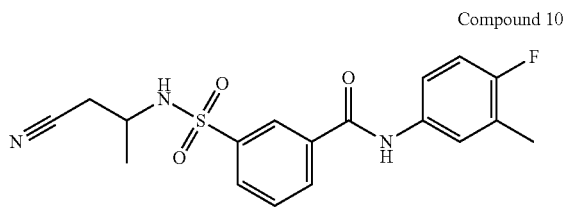 [SMILES: Cc1cc(NC(=O)c2cccc(S(=O)(=O)NC(C)CC#N)c2)ccc1F]

3-[(4-fluoro-3-methyl-phenyl)carbamoyl]benzenesulfonyl chloride (400 mg, 1.22 mmol) and 3-aminobutanenitrile (102 mg, 1.22 mmol) were dissolved in CH$_2$Cl$_2$ (4 mL). DIPEA was added drop wise at 0°. The mixture was stirred for 8 hours at 25° C. and next washed with saturated citric acid (10 mL), saturated aqueous NaHCO$_3$ (10 mL) and brine. After drying over Na$_2$SO$_4$, the solvent was removed in vacuo and the obtained crude was purified by preparative high-performance liquid chromatography (column: Luna 150*30 mm*5 u, mobile phase: CH$_3$CN in water (0.5% NH$_4$HCO$_3$) from 38% to 68%). The relevant fraction were concentrated in vacuo and the residual aqueous layer was lyophilized to dryness resulting in compound 10 (300 mg). Method A; Rt: 5.22 min. m/z: 376.3 (M+H)$^+$ Exact mass: 375.1. $^1$H NMR (400 MHz, DMSO-d$_6$) δ ppm 0.98 (d, J=6.8 Hz, 3H) 2.26 (d, J=1.3 Hz, 3H) 2.62 (dd, J=16.8, 5.8 Hz, 1H) 2.71 (dd, J=16.6, 5.3 Hz, 1H) 3.45-3.55 (m, 1H) 7.16 (t, J=9.3 Hz, 1H) 7.56-7.62 (m, 1H) 7.68 (dd, J=6.8, 2.3 Hz, 1H) 7.78 (t, J=8.0 Hz, 1H) 8.00-8.07 (m, 1H) 8.16-8.28 (m, 2H) 8.38 (t, J=1.5 Hz, 1H) 10.49 (s, 1H). Racemic mixture 10 was separated in enantiomers 10a (Method F; Rt: 0.90 min. m/z: 376.2 (M+H)$^+$ Exact mass: 375.1), and 10b (Method F; Rt: 0.90 min. m/z: 376.1 (M+H)$^+$ Exact mass: 375.1 by preparative SFC (Stationary phase: Chiralpak Diacel AD 30×250 mm), Mobile phase: CO$_2$, MeOH with 0.4% iPrNH$_2$). SFC; Column: AD-H (diacel) 250 mm×4.6 mm, Flow: 5 ml/min; Mobile phase: 35% MeOH (containing 0.2% iPrNH$_2$) hold 4.00 min, up to 50% in 1 minute and hold 2.00 minutes at 50%; Temperature: 40° C. Rt: 10a (1.7 min), 10b (2.3 min).

Alternative Synthesis of Compound 10a:

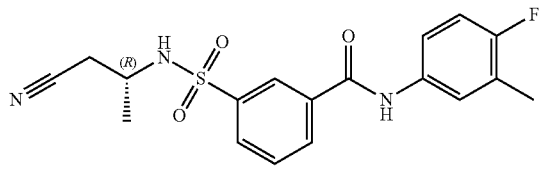

Compound 4a (1 g, 2.73 mmol) was dissolved in dichloromethane (50 mL) and diisopropylethylamine (941 µL, 5.46 mmol) was added. This mixture was cooled in an ice bath and stirred for 20 minutes. Then methanesulfonyl chloride (317 ptL, 4.09 mmol) in dichloromethane (25 mL) was added slowly and drop wise over 30 minutes. Cooling was continued for another 30 minutes. The mixture was quenched with water (75 mL), the layers were separated and the aqueous layer was extracted with dichloromethane (2×75 mL). The combined organics were washed with HCL (1M, 75 mL) and NaHCO$_3$ (sat, 10 mL). The combined organics were dried on Na$_2$SO$_4$, filtered and concentrated in vacuo. The obtained residue was purified by silica gel column chromatography using gradient elution from heptane to EtOAc. (100:0 to 0:100) yielding [(2R)-2-[[3-[(4-fluoro-3-methyl-phenyl)carbamoyl]phenyl]sulfonylamino]propyl] methanesulfonate (916 mg) as a white powder. Sodium cyanide (33.1 mg, 67 mmol) was suspended in DMSO (5 mL) and this was warmed to 40° C. A solution of [(2R)-2-[[3-[(4-fluoro-3-methyl-phenyl)carbamoyl]phenyl]sulfonylamino]propyl]methanesulfonate (100 mg, 0.22 mmol) in DMSO (5 mL) was added drop wise. After 1 hour the solution was cooled to room temperature and then water (12 mL) was added. The resulting mixture was extracted using diethylether (2×15 mL). The combined extracts were dried on MgSO$_4$, filtered and concentrated in vacuo. The obtained residue was purified by silica gel column chromatography using gradient elution from heptane to EtOAc. (100:0 to 0:100). The combined fractions were concentrated in vacuo and dried in a vacuum oven at 55° C. for 24 hours yielding compound 10a as a white power (21.4 mg).

Synthesis of 3-[(4-fluoro-3-methyl-phenyl)carbamoyl]benzenesulfonyl Chloride 3-(chlorosulfonyl)benzoyl chloride (32.4 g, 135.6 mmol) was dissolved in dry toluene (250 mL) in a 1 L multi neck flask. The mixture was stirred with an overhead stirrer (240 rpm) and brought to a gentle reflux under a nitrogen flow. 4-fluoro-3-methyl-aniline (15.4 g, 123.3 mmol) dissolved in dry toluene (100 mL) was added drop wise via a syringe pump at a flow of 2 mL/min. After complete addition the reaction was heated for another 30 minutes and then slowly cooled to room temperature. After over night stirring at 60 rpm the reaction mixture was cooled with an ice bath and diisopropylether (100 mL) was added. The precipitate was filtered off, triturated with diisopropylether and dried in a vacuum oven, resulting in a solid (30.9 g) The solid was recrystallized from toluene (200 mL) resulting in 3-[(4-fluoro-3-methyl-phenyl)carbamoyl]benzenesulfonyl chloride (22.9 g).

Compound 11

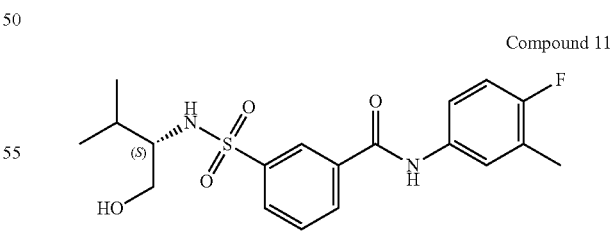

Synthesis following procedure S1 with (S)-(+)-2-amino-3-methyl-1-butanol as amine, workup W1. Method G; Rt: 1.66 min. m/z: 395.0 (M+H)$^+$ Exact mass: 394.1. $^1$H NMR (400 MHz, DMSO-d$_6$) ppm 0.73 (d, J=6.8 Hz, 3H), 0.76 (d, J=6.8 Hz, 3H), 1.77-1.91 (m, 1H), 2.25 (d, J=1.8 Hz, 3H), 2.93-3.06 (m, 1H), 3.10-3.26 (m, 2H), 4.49 (t, J=5.4 Hz, 1H), 7.14 (t, J=9.2 Hz, 1H), 7.49 (d, J=8.6 Hz, 1H), 7.56-7.63 (m, 1H), 7.68 (dd, J=7.3, 2.4 Hz, 1H), 7.73 (t, J=7.8 Hz, 1H), 7.97-8.03 (m, 1H), 8.13-8.20 (m, 1H), 8.37 (t, J=1.7 Hz, 1H), 10.44 (s, 1H)

Compound 12

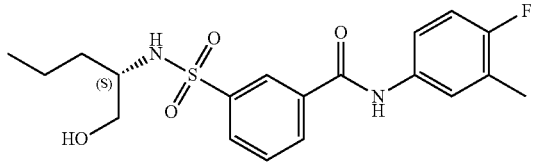

Synthesis following procedure S1 with (S)-(+)-2-amino-1-pentanol as amine, workup W1. Method F; Rt: 0.94 min. m/z: 412.2 (M+NH$_4$)$^+$ Exact mass: 394.1.

Compound 13

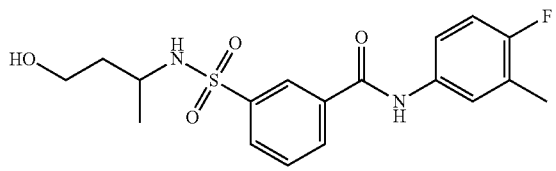

Synthesis following procedure S1 with 3-amino-3-methylpropan-1-ol as amine, workup W2. Method F; Rt: 0.85 min. m/z: 381.1 (M+H)$^+$ Exact mass: 380.1.

Compound 14

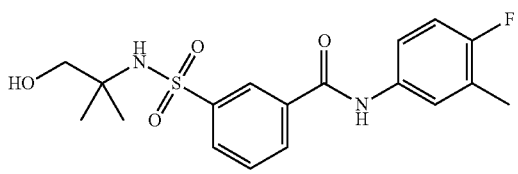

Synthesis following procedure S1 with 2-amino-2-methyl-1-propanol as amine, workup W1. Method F; Rt: 0.88 min. m/z: 398.1 (M+NH$_4$)$^+$ Exact mass: 380.1. $^1$H NMR (400 MHz, DMSO-d$_6$) δ ppm 1.03 (s, 6H), 2.25 (d, J=1.8 Hz, 3H), 3.21 (d, J=5.7 Hz, 2H), 4.77 (t, J=5.8 Hz, 1H), 7.14 (t, J=9.2 Hz, 1H), 7.46 (s, 1H), 7.56-7.63 (m, 1H), 7.68 (dd, J=7.2, 2.3 Hz, 1H), 7.73 (t, J=7.8 Hz, 1H), 8.00-8.06 (m, 1H), 8.16 (dt, J=7.8, 1.3 Hz, 1H), 8.39 (t, J=1.7 Hz, 1H), 10.44 (s, 1H)

Compound 15

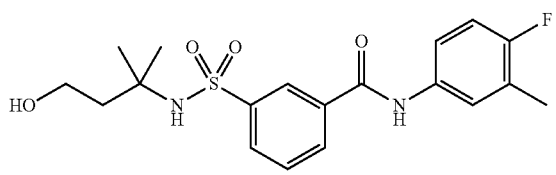

Synthesis following procedure S2 with 3-amino-3-methyl-1-butanol as amine, workup W3. Method F; Rt: 0.90 min. m/z: 412.2 (M+NH$_4$)$^+$ Exact mass: 394.1.

$^1$H NMR (400 MHz, CHLOROFORM-d) δ ppm 1.28 (s, 6H), 1.75 (t, J=5.8 Hz, 2H), 2.07 (t, J=4.5 Hz, 1H), 2.30 (d, J=1.8 Hz, 3H), 3.85 (td, J=5.8, 4.5 Hz, 2H), 6.10 (s, 1H), 7.01 (t, J=8.9 Hz, 1H), 7.37-7.44 (m, 1H), 7.53 (dd, J=6.5, 2.5 Hz, 1H), 7.61 (t, J=7.8 Hz, 1H), 7.99-8.12 (m, 2H), 8.15 (s, 1H), 8.37 (t, J=1.7 Hz, 1H)

Compound 16

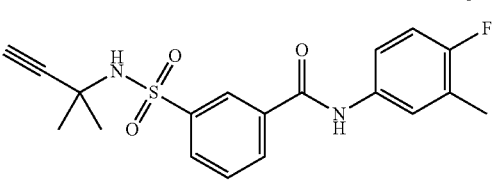

Synthesis following procedure S4 with 3-amino-3-methyl-1-butyne as amine, workup W4. Method F; Rt: 1.01 min. m/z: 392.3 (M+NH$_4$)$^+$ Exact mass: 374.1.

Compound 17

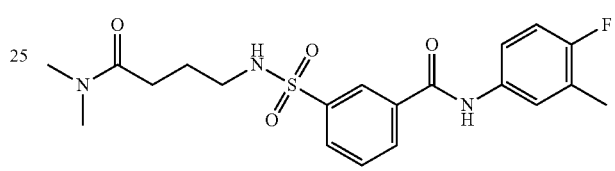

Synthesis following procedure S2 with 4-amino-N,N-dimethyl-butanamide hydrochloride as amine, workup W3. Method F; Rt: 0.87 min. m/z: 422.2 (M+H)$^+$ Exact mass: 421.2. $^1$H NMR (400 MHz, CHLOROFORM-d) δ ppm 1.74-1.82 (m, 2H) 2.29 (d, J=2.0 Hz, 3H) 2.31-2.37 (m, 2H) 2.85 (s, 3H) 2.94 (s, 3H) 3.04-3.10 (m, 2H) 5.70 (t, J=5.5 Hz, 1H) 6.99 (t, J=9.0 Hz, 1H) 7.43-7.50 (m, 1H) 7.58 (dd, J=6.7, 2.5 Hz, 1H) 7.63 (t, J=7.8 Hz, 1H) 8.02 (ddd, J=7.8, 1.8, 1.5 Hz, 1H) 8.17 (ddd, J=7.9, 1.8, 1.5 Hz, 1H) 8.37 (t, J=1.8 Hz, 1H) 8.80 (bs, 1H)

Compound 18

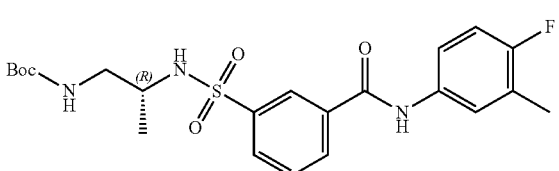

Synthesis following procedure S4 (reaction time: 20 hours instead of 3 hours) with N-[(2R)-2-aminopropyl]-carbamic acid 1,1-dimethylethyl ester hydrochloride as amine, workup W4. Method F; Rt: 1.06 min. m/z: 466.2 (M+H)$^+$ Exact mass: 465.2.

$^1$H NMR (400 MHz, DMSO-d$_6$) δ ppm 0.86 (d, J=6.6 Hz, 3H), 1.34 (s, 9H), 2.26 (d, J=1.8 Hz, 3H), 2.71-3.02 (m, 2H), 3.17-3.33 (m, 1H), 6.30-6.93 (m, 1H), 7.14 (t, J=9.1 Hzj 1H), 7.57-7.65 (m, 1H), 7.66-7.74 (m, 2H), 7.76 (t, J=7.7 Hz, 1H), 7.98-8.08 (m, 1H), 8.16-8.27 (m, 1H), 8.39 (s, 1H), 10.46 (s, 1H).

Compound 19

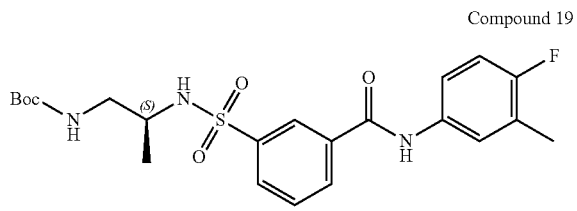

Synthesis following procedure S4 (reaction time: 20 hours instead of 3 hours) with N-[(2S)-2-aminopropyl]-carbamic acid 1,1-dimethylethyl ester hydrochloride as amine, workup W4. Method F; Rt: 1.06 min. m/z: 466.2 (M+H)⁺ Exact mass: 465.2

Compound 1a

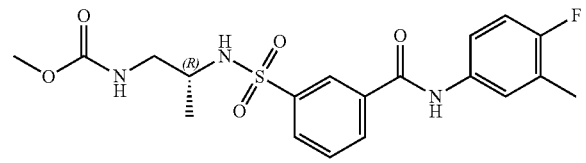

Compound 18 (203 mg) was dissolved in dichloromethane (5 mL) and then HCl (6 M in iPrOH) (726 μL) was added. The mixture was stirred at room temperature for 5 hours and next concentrated under reduced pressure. The obtained oil was dissolved in dichloromethane (5 mL). Diisopropylethylamine (309 μL, 1.79 mmol) was added followed methyl chloroformate (52 μL, 0.67 mmol). The resulting mixture was stirred for 1 hour and next injected as such on a silica plug and purified using flash chromatography (gradient elution: EtOAc-heptane 0:100 to 100:0). The fractions were concentrated under reduced pressure and the obtained residue was dried in vacuo at 55° C. for 20 hours resulting in compound 1a as a white powder. Method F; Rt: 0.89 min. m/z: 441.3 (M+NH₄)⁺ Exact mass: 423.1. ¹H NMR (400 MHz, DMSO-d₆) δ ppm 0.84-0.89 (m, 3H), 2.25 (d, J=1.8 Hz, 3H), 2.78-2.99 (m, 2H), 3.19-3.29 (m, 1H), 3.44 (s, 3H), 7.02 (t, J=5.8 Hz, 1H), 7.14 (t, J=9.1 Hz, 1H), 7.55-7.63 (m, 1H), 7.68 (dd, J=6.8, 2.4 Hz, 1H), 7.71-7.82 (m, 2H), 7.92-8.08 (m, 1H), 8.15-8.23 (m, 1H), 8.36 (t, J=1.7 Hz, 1H), 10.45 (s, 1H).

Compound 1b

Compound 1b was prepared similarly as described for 1a, starting from compound 19 instead of compound 18. Method F; Rt: 0.89 min. m/z: 424.1 (M+H)⁺ Exact mass: 423.1.

Compound 20

Diisopropylethylamine (92 μL, 0.54 mmol) was added to a solution of compound 2 (52 mg) in dichloromethane (5 mL), followed by methyl chloroformate (15.5 μL, 0.2 mmol). The resulting mixture was stirred for 1 hour. Workup W4. Method F; Rt: 0.95 min. m/z: 455.1 (M+NH₄)⁺ Exact mass: 437.1. ¹H NMR (400 MHz, DMSO-d₆) δ ppm 0.76-1.05 (m, 3H), 2.17-2.31 (m, 3H), 2.61-2.79 (m, 3H), 2.95-3.21 (m, 2H), 3.40-3.55 (m, 4H), 7.14 (t, J=9.1 Hz, 1H), 7.56-7.64 (m, 1H), 7.68 (dd, J=6.9, 2.3 Hz, 1H), 7.71-7.91 (m, 2H), 7.93-8.01 (m, 1H), 8.14-8.24 (m, 1H), 8.34 (t, J=1.5 Hz, 1H), 10.45 (s, 1H).

Compound 21

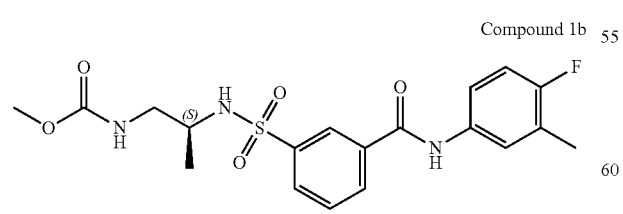

Synthesis following procedure S4 with 6-amino-2-methyl-2-heptanol as amine, workup W4. Method F; Rt: 0.99 min. m/z: 454.2 (M+NH₄)⁺ Exact mass: 436.2.

The racemic compound 21 was separated in enantiomers 21a and 21b by preparative SFC (Stationary phase: Chiralpak Diacel AD 30×250 mm), Mobile phase: CO₂, MeOH with 0.4% iPrNH₂), SFC: Column: AD-H 250 mm×4.6 mm, Flow: 5 mL/min, Mobile phase: 25% EtOH (containing 0.2% iPrNH₂) hold 4 min, increased to 50% in 1 min, hold 2 min at 50%, Temperature: 40° C. Rt: 21a (1.9 min; (Method G; Rt: 1.76 min. m/z: 437.1 (M+H)⁺ Exact mass: 436.2)); 21b (2.6 min; (Method G; Rt: 1.76 min. m/z: 437.0 (M+H)⁺ Exact mass: 436.2)). ¹H NMR (400 MHz, DMSO-d₆) δ ppm 0.90 (d, J=6.6 Hz, 3H), 0.97 (s, 6H), 1.04-1.31 (m, 6H), 2.25 (d, J=1.8 Hz, 3H), 3.13-3.24 (m, 1H), 3.98 (s, 1H), 7.14 (t, J=9.2 Hz, 1H), 7.55-7.63 (m, 1H), 7.63-7.69 (m, 2H), 7.75 (t, J=7.8 Hz, 1H), 7.96-8.03 (m, 1H), 8.19 (dt, J=7.9, 1.2 Hz, 1H), 8.37 (t, J=1.7 Hz, 1H), 10.45 (s, 1H)

Compound 22

Synthesis following procedure S4 with (2R)-2-aminopropanamide as amine, workup W1. Method F; Rt: 0.77 min. m/z: 397.2 (M+NH₄)⁺ Exact mass: 379.1. ¹H NMR (400 MHz, DMSO-d₆) δ ppm 1.08 (d, J=7.0 Hz, 3H), 2.25 (d, J=1.8 Hz, 3H), 3.75 (q, J=7.0 Hz, 1H), 6.97 (br. s., 1H), 7.14 (t, J=9.1 Hz, 1H), 7.26 (br. s., 1H), 7.55-7.64 (m, 1H), 7.68

(dd, J=7.0, 2.4 Hz, 1H), 7.73 (t, J=7.8 Hz, 1H), 7.96-8.01 (m, 1H), 8.05 (br. s., 1H), 8.17 (dt, J=8.0, 1.2 Hz, 1H), 8.36 (t, J=1.7 Hz, 1H), 10.42 (s, 1H).

Compound 23

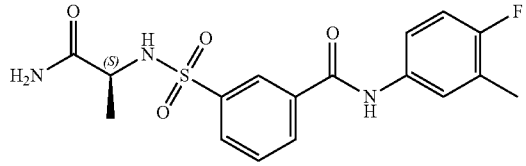

Synthesis following procedure S4 with (2S)-2-aminopropanamide as amine, workup W1. Method F; Rt: 0.78 min. m/z: 397.1 (M+NH$_4$)$^+$ Exact mass: 379.1.

Compound 24

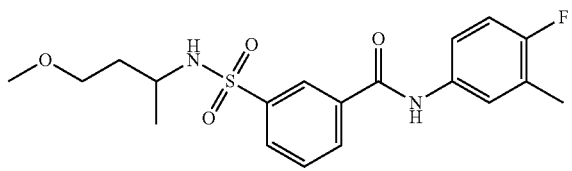

Synthesis following procedure S4 with 4-methoxy-2-butanamine as amine, workup W4. Method F; Rt: 0.98 min. m/z: 412.2 (M+NH$_4$)$^+$ Exact mass: 394.1.

$^1$H NMR (400 MHz, DMSO-d$_6$) δ ppm 0.92 (d, J=6.6 Hz, 3H), 1.43-1.61 (m, 2H), 2.25 (d, J=1.8 Hz, 3H), 3.05 (s, 3H), 3.10-3.24 (m, 2H), 3.24-3.31 (m, 1H), 7.14 (t, J=9.2 Hz, 1H), 7.54-7.64 (m, 1H), 7.64-7.73 (m, 2H), 7.76 (t, J=7.8 Hz, 1H), 7.96-8.03 (m, 1H), 8.20 (dt, J=7.9, 1.3 Hz, 1H), 8.36 (t, J=1.7 Hz, 1H), 10.47 (s, 1H)

Compound 25

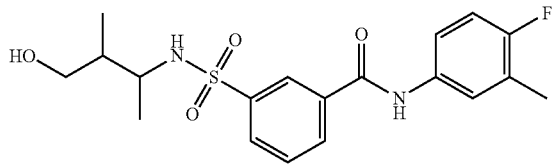

Synthesis following procedure S4 with 3-amino-2-methyl-1-butanol as amine, workup W4. Method F; Rt: 0.89 min. m/z: 412.2 (M+NH$_4$)$^+$ Exact mass: 394.1

$^1$H NMR (400 MHz, DMSO-d$_6$) δ ppm 0.68-0.87 (m, 6H), 1.54-1.68 (m, 1H), 2.25 (d, J=1.8 Hz, 3H), 3.09-3.30 (m, 2H), 3.30-3.40 (m, 1H), 4.26-4.55 (m, 1H), 7.14 (t, J=9.2 Hz, 1H), 7.44-7.65 (m, 1H), 7.56-7.63 (m, 1H), 7.68 (dd, J=7.2, 2.5 Hz, 1H), 7.75 (t, J=7.8 Hz, 1H), 7.97-8.04 (m, 1H), 8.19 (d, J=7.7 Hz, 1H), 8.36 (t, J=1.5 Hz, 1H), 10.46 (br. s., 1H)

Compound 26

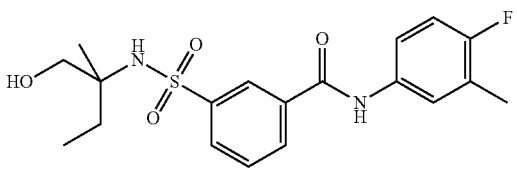

Synthesis following procedure S4 with 2-amino-2-methyl-1-butanol as amine, workup W4. Method F; Rt: 0.92 min. m/z: 412.2 (M+NH$_4$)$^+$ Exact mass: 394.1.

$^1$H NMR (400 MHz, DMSO-d$_6$) δ ppm 0.71 (t, J=7.4 Hz, 3H), 0.98 (s, 3H), 1.47 (q, J=7.3 Hz, 2H), 2.25 (d, J=1.5 Hz, 3H), 3.19-3.27 (m, 2H), 4.66 (t, J=5.5 Hz, 1H), 7.14 (t, J=9.1 Hz, 1H), 7.34 (s, 1H), 7.55-7.62 (m, 1H), 7.68 (dd, J=7.2, 2.3 Hz, 1H), 7.72 (t, J=7.8 Hz, 1H), 8.00-8.06 (m, 1H), 8.12-8.18 (m, 1H), 8.38 (t, J=1.7 Hz, 1H), 10.44 (s, 1H)

Compound 27

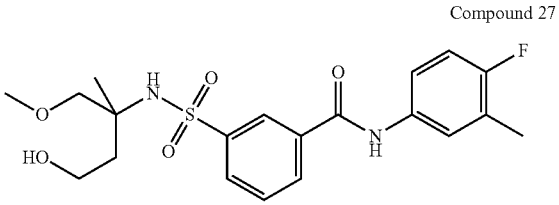

Synthesis following procedure S4 with 3-amino-4-methoxy-3-methyl-1-butanol as amine, workup W4. Method F; Rt: 0.89 min. m/z: 425.2 (M+H)$^+$ Exact mass: 424.2. $^1$H NMR (400 MHz, DMSO-d$_6$) δ ppm 1.07 (s, 3H), 1.58-1.79 (m, 2H), 2.25 (d, J=1.5 Hz, 3H), 2.99 (s, 3H), 3.12-3.19 (m, 2H), 3.40-3.49 (m, 2H), 4.42 (t, J=4.6 Hz, 1H), 7.14 (t, J=9.1 Hz, 1H), 7.53-7.63 (m, 2H), 7.68 (dd, J=7.0, 2.4 Hz, 1H), 7.72 (t, J=7.8 Hz, 1H), 7.99-8.05 (m, 1H), 8.13-8.19 (m, 1H), 8.38 (t, J=1.7 Hz, 1H), 10.44 (s, 1H)

Compound 28

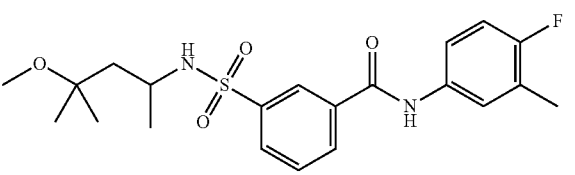

Synthesis following procedure S4 with 4-methoxy-4-methyl-2-pentanamine as amine, workup W4. Method F; Rt: 1.09 min. m/z: 423.2 (M+H)$^+$ Exact mass: 422.2.

$^1$H NMR (400 MHz, DMSO-d$_6$) δ ppm 0.93 (d, J=6.4 Hz, 3H), 0.96 (s, 3H), 1.01 (s, 3H), 1.44-1.58 (m, 2H), 2.25 (d, J=1.8 Hz, 3H), 2.98 (s, 3H), 3.32-3.41 (m, 1H), 7.14 (t, J=9.2 Hz, 1H), 7.53-7.64 (m, 2H), 7.68 (dd, J=7.0, 2.4 Hz, 1H), 7.76 (t, J=7.8 Hz, 1H), 7.97-8.03 (m, 1H), 8.20 (dt, J=7.9, 1.3 Hz, 1H), 8.34-8.39 (m, 1H), 10.47 (s, 1H)

Compound 29

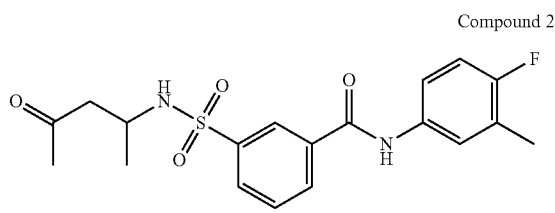

Synthesis following procedure S4 with 4-aminopentan-2-one hydrochloride as amine, workup W4. Method F; Rt: 0.92 min. m/z: 410.2 (M+NH₄)⁺ Exact mass: 392.1.

¹H NMR (400 MHz, DMSO-d₆) δ ppm 0.89 (d, J=6.6 Hz, 3H), 2.01 (s, 3H), 2.25 (d, J=1.8 Hz, 3H), 2.52 (d, J=7.7 Hz, 2H), 3.53-3.66 (m, 1H), 7.14 (t, J=9.2 Hz, 1H), 7.55-7.65 (m, 1H), 7.68 (dd, J=7.2, 2.3 Hz, 1H), 7.76 (t, J=7.8 Hz, 1H), 7.82 (d, J=5.9 Hz, 1H), 7.95-8.01 (m, 1H), 8.20 (dt, J=8.0, 1.2 Hz, 1H), 8.35 (t, J=1.7 Hz, 1H), 10.46 (s 1H)

Compound 30

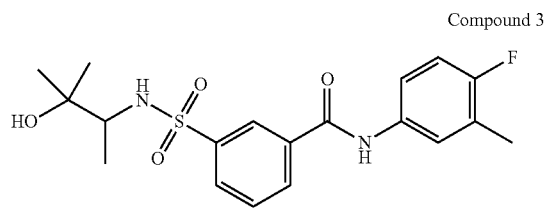

Synthesis following procedure S4 with 3-amino-2-methyl-2-butanol as amine, workup W4. Method F; Rt: 0.90 min. m/z: 412.2 (M+NH₄)⁺ Exact mass: 394.1.

¹H NMR (400 MHz, DMSO-d₆) δ ppm 0.76 (d, J=6.6 Hz, 3H), 0.99 (s, 3H), 1.06 (s, 3H), 2.26 (d, J=1.8 Hz, 3H), 3.00-3.12 (m, 1H), 4.29 (s, 1H), 7.14 (t, J=9.1 Hz, 1H), 7.45 (br. s., 1H), 7.56-7.65 (m, 1H), 7.69 (dd, J=7.2, 2.3 Hz, 1H), 7.76 (t, J=7.8 Hz, 1H), 7.99-8.07 (m, 1H), 8.19 (dt, J=7.9, 1.2 Hz, 1H), 8.39 (t, J=1.7 Hz, 1H), 10.47 (s, 1H)

Compound 31

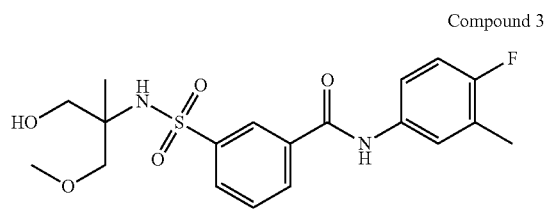

Synthesis following procedure S4 with 2-amino-3-methoxy-2-methyl-1-propanol as amine, workup W4. Method F; Rt: 0.89 min. m/z: 428.1 (M+NH₄)⁺ Exact mass: 410.1. ¹H NMR (400 MHz, DMSO-d₆) δ ppm 1.02 (s, 3H), 2.25 (d, J=1.8 Hz, 3H), 3.01 (s, 3H), 3.10-3.24 (m, 2H), 3.24-3.30 (m, 1H), 3.33-3.39 (m, 1H), 4.73 (t, J=5.7 Hz, 1H), 7.14 (t, J=9.1 Hz, 1H), 7.42 (s, 1H), 7.54-7.63 (m, 1H), 7.64-7.69 (m, 1H), 7.72 (t, J=7.9 Hz, 1H), 8.02-8.07 (m, 1H), 8.15 (dt, J=8.1, 1.2 Hz, 1H), 8.39 (t, J=1.7 Hz, 1H), 10.43 (s, 1H)

Compound 32

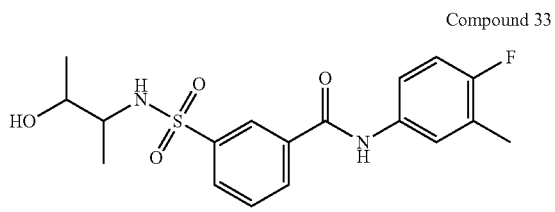 [SMILES: Cc1cc(NC(=O)c2cccc(S(=O)(=O)NC(C)C(C)O)c2)ccc1F]

Synthesis following procedure S4 with 2-amino ethylmethylsulfone hydrochloride as amine, workup W4. Method F; Rt: 0.83 min. m/z: 415.3 (M+H)⁺ Exact mass: 414.1. ¹H NMR (400 MHz, DMSO-d₆) δ ppm 2.25 (d, J=1.8 Hz, 3H), 3.01 (s, 3H), 3.15-3.22 (m, 2H), 3.24-3.29 (m, 2H), 7.14 (t, J=9.1 Hz, 1H), 7.55-7.64 (m, 1H), 7.67 (dd, J=7.0, 2.2 Hz, 1H), 7.79 (t, J=7.8 Hz, 1H), 7.99-8.04 (m, 1H), 8.09 (br. s., 1H), 8.23 (dt, J=8.1, 1.2 Hz, 1H), 8.36 (t, J=1.7 Hz, 1H), 10.48 (s, 1H)

Compound 33

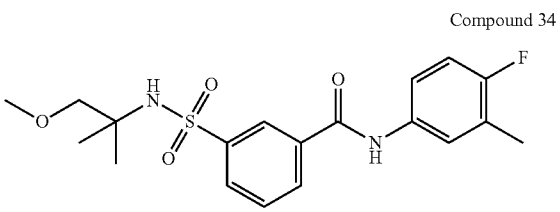

Synthesis following procedure S4 with 3-aminobutan-2-ol as amine, workup W4. Method F; Rt: 0.86 min. m/z: 398.2 (M+NH₄)⁺ Exact mass: 380.1.

¹H NMR (400 MHz, DMSO-d₆) δ ppm 0.77-0.86 (m, 3H), 0.90-0.99 (m, 3H), 2.25 (d, J=1.8 Hz, 3H), 2.96-3.20 (m, 1H), 3.37-3.61 (m, 1H), 4.54-4.65 (m, 1H), 7.14 (t, J=9.2 Hz, 1H), 7.50-7.64 (m, 2H), 7.68 (dd, J=7.0, 2.2 Hz, 1H), 7.72-7.79 (m, 1H), 7.99-8.06 (m, 1H), 8.19 (dt, J=7.9, 1.2 Hz, 1H), 8.35-8.41 (m, 1H), 10.46 (br. s., 1H)

Compound 34

Synthesis following procedure S4 with 1-methoxy-2-methyl-2-propanamine as amine, workup W4. Method F; Rt: 1.02 min. m/z: 412.2 (M+NH₄)⁺ Exact mass: 394.1. ¹H NMR (400 MHz, DMSO-d₆) δ ppm 1.08 (s, 6H), 2.25 (d, J=1.8 Hz, 3H), 3.05 (s, 3H), 3.13 (s, 2H), 7.14 (t, J=9.2 Hz, 1H), 7.55-7.63 (m, 1H), 7.63-7.70 (m, 2H), 7.73 (t, J=7.8 Hz, 1H), 8.00-8.06 (m, 1H), 8.13-8.19 (m, 1H), 8.39 (t, J=1.7 Hz, 1H), 10.44 (s, 1H)

Compound 35

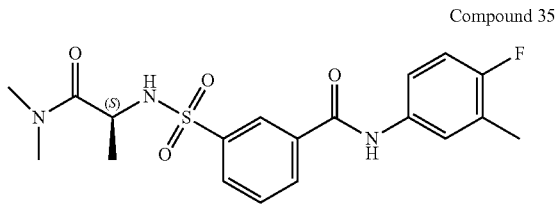

To a solution of L-alanine (130.5 mg, 1.46 mmol) in NaOH (1M in H₂O) (1.53 mL, 1.53 mmol) at 0° C., acetone (11.5 mL, 156.1 mmol) was added, followed by 3-[(4-fluoro-3-methyl-phenyl)carbamoyl]benzenesulfonyl chloride (500 mg, 1.53 mmol) and DIPEA (788.65 µl, 4.58 mmol). The mixture was stirred for 30 minutes at room temperature. The resulting mixture was washed with diethylether (3×10 mL) and the combined organic washings were extracted with NaOH (1M/2×10 mL). The combined basic aqueous layers were acidified to pH 1 using concentrated hydrochloric acid. A precipitation was formed. The mixture was extracted with ethyl acetate (3×25 mL). The combined extracts were washed with brine, dried on MgSO₄, filtered and concentrated under reduced pressure. (2S)-2-[[3-[(4-fluoro-3-methyl-phenyl)carbamoyl]phenyl]sulfonylamino]propanoic acid (0.577 g) was obtained as a slightly pink powder and was used as such. Method G; Rt: 1.16 min. m/z: 381.0 (M+H)⁺ Exact mass: 380.1.

(2S)-2-[[3-[(4-fluoro-3-methyl-phenyl)carbamoyl]phenyl]sulfonylamino]propanoic acid (0.2 g, 0.49 mmol), HATU (0.21 g, 0.54 mmol), DIPEA (0.26 mL, 1.48 mmol) and dichloromethane (10 mL) were stirred in a closed vessel at room temperature. 3 drops of dimethylamine were added and the vessel was closed. The mixture was stirred at room temperature for 2 hours. An extra equivalent of HATU, 2 extra equivalents of DIPEA, and 3 drops of dimethylamine were added and the mixture was stirred for another 2 hours. Then the mixture was heated to 50° C. and stirred for 2 hours. The mixture was concentrated to dryness under reduced pressure and purified by Prep HPLC on (RP SunFire Prep C18 OBD-10 m, 30×150 mm). Mobile phase (0.25% NH₄HCO₃ solution in water, acetonitrile). The desired fractions were concentrated under reduced pressure, co-evaporated with methanol (2×10 mL) and dried in vacuo, resulting in compound 35 (40 mg) as a white powder. Method F; Rt: 0.88 min. m/z: 425.2 (M+NH₄)⁺ Exact mass: 407.1. ¹H NMR (400 MHz, DMSO-d₆) δ ppm 1.07 (d, J=6.8 Hz, 3H), 2.25 (d, J=1.8 Hz, 3H), 2.57 (s, 3H), 2.94 (s, 3H), 4.31-4.40 (m, 1H), 7.15 (t, J=9.2 Hz, 1H), 7.57-7.64 (m, 1H), 7.65-7.70 (m, 1H), 7.72 (t, J=7.8 Hz, 1H), 7.90-8.00 (m, 1H), 8.07 (br. s., 1H), 8.12-8.21 (m, 1H), 8.31 (t, J=1.7 Hz, 1H), 10.43 (s, 1H)

Compound 36

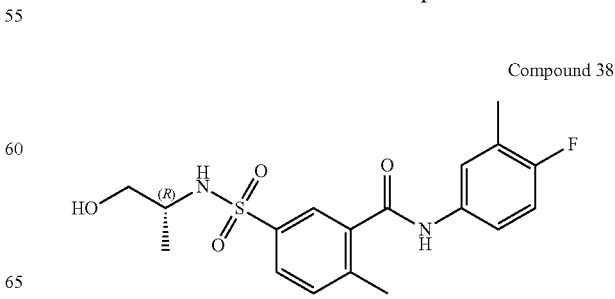

Synthesis following procedure S4 (20 hours instead of 3 hours reaction time) with 4-amino-4-methyl-2-pentanol as amine, workup W4. Method F; Rt: 0.99 min. m/z: 426.2 (M+NH₄)⁺ Exact mass: 408.2. ¹H NMR (400 MHz, DMSO-d₆) δ ppm 0.99-1.07 (m, 3H), 1.13 (s, 3H), 1.15-1.22 (m, 3H), 1.43-1.58 (m, 2H), 2.20-2.31 (m, 3H), 3.75-3.95 (br. s., 1H), 4.73 (d, J=4.2 Hz, 1H), 7.14 (t, J=9.1 Hz, 1H), 7.55-7.66 (m, 2H), 7.70 (dd, J=7.2, 2.3 Hz, 1H), 7.74 (t, J=7.8 Hz, 1H), 7.95-8.09 (m, 1H), 8.15-8.23 (m, 1H), 8.39 (t, J=1.7 Hz, 1H), 10.46 (s, 1H)

Compound 37

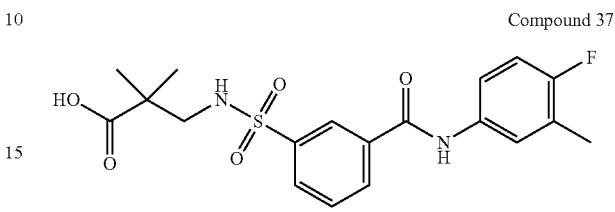

Synthesis following procedure S4 (reaction time: 20 hours instead of 3 hours) with 3-amino-2,2-dimethyl-propanoic acid as amine, workup W4. Method F; Rt: 0.70 min. m/z: 426.2 (M+NH₄)⁺ Exact mass: 408.1. ¹H NMR (400 MHz, DMSO-d₆) δ ppm 1.07 (s, 6H), 2.27 (d, J=1.0 Hz, 3H), 2.80 (s, 2H), 2.97-3.54 (br. s, 2H), 7.13 (t, J=9.2 Hz, 1H), 7.55-7.65 (m, 1H), 7.67-7.83 (m, 2H), 7.99 (m, J=8.1 Hz, 1H), 8.17 (m, J=7.9 Hz, 1H), 8.37 (s, 1H), 10.67 (br. s., 1H).

Synthesis of 5-chlorosulfonyl-2-methyl-benzoyl chloride and 3-[(4-fluoro-3-methyl-phenyl)carbamoyl]-4-methyl-benzenesulfonyl Chloride 5-(chlorosulfonyl)-2-methylbenzoic acid (10 g, 42.61 mmol) was dissolved in dichloromethane (200 mL). N,N-dimethylformamide (166 µL, 2.13 mmol) was added and the mixture was stirred at room temperature under a nitrogen atmosphere. Oxalyl chloride (18.3 mL, 213 mmol) was added in four portions over one hour.

The resulting mixture was stirred for one hour at room temperature. The mixture was concentrated in vacuo and co-evaporated twice using toluene (2×100 mL) yielding 5-chlorosulfonyl-2-methyl-benzoyl chloride as a yellow oil which was used as such. 5-chlorosulfonyl-2-methyl-benzoyl chloride (10.7 g, 42.3 mmol) was dissolved in toluene (220 mL) and this was heated to reflux and stirred under a gentle flow of nitrogen.

4-fluoro-3-methylaniline (4.76 g, 38.1 mmol) in toluene (80 mL) was added drop wise using a syringe pump (0.8 mL/min). The resulting mixture was stirred for 30 minutes while heating was continued. Then the mixture was cooled to room temperature. A precipitation was formed and collected on a glass filter. The obtained solid was dried in vacuo at 55° C., yielding 3-[(4-fluoro-3-methyl-phenyl)carbamoyl]-4-methyl-benzenesulfonyl chloride (10.4 g) as a solid which was used as such in the next step.

Compound 38

A solution of D-alaninol (0.33 g, 4.39 mmol) and diisopropylethylamine (1.26 mL, 7.31 mmol) in dichloromethane (10 mL) was added to a solution of 3-[(4-fluoro-3-methylphenyl)carbamoyl]-4-methyl-benzenesulfonyl chloride (1 g, 2.93 mmol) in dichloromethane (10 mL). The resulting mixture was stirred for 1 hour at room temperature. The mixture was quenched using HCl (aq, 14.6 mL, 14.6 mmol). A precipitation was formed between the two layers. This precipitation was collected on a glass filter and recrystallised from Diisopropylether/acetonitrile. The crystals were collected and dried in a vacuum oven at 55° C. for 24 hours yielding compound 38 (643 mg) as bright white crystals. Method F; Rt: 0.85 min. m/z: 398.2 (M+NH$_4$)$^+$ Exact mass: 380.1. $^1$H NMR (400 MHz, DMSO-d$_6$) δ ppm 0.92 (d, J=6.2 Hz, 3H), 2.24 (d, J=1.5 Hz, 3H), 2.44 (s, 3H), 3.05-3.18 (m, 2H), 3.25-3.38 (m, 1H), 4.60-4.78 (m, 1H), 7.13 (t, J=9.2 Hz, 1H), 7.45-7.61 (m, 3H), 7.60-7.70 (m, 1H), 7.77-7.86 (m, 2H), 10.44 (s, 1H)

Compound 39

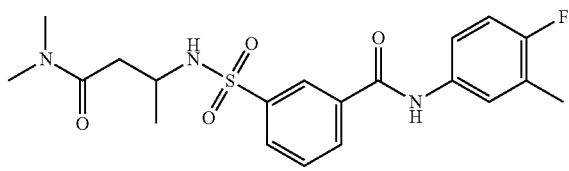

Compound 39 was prepared similarly as described for compound 6, using 3-amino-N,N-dimethyl-butanamide hydrochloride instead of the TFA salt of 4-amino-N,N-dimethyl-pentanamide. Method E; Rt: 4.81 min. m/z: 422.1 (M+H)$^+$ Exact mass: 421.1. $^1$H NMR (400 MHz, DMSO-d$_6$) δ ppm 0.96 (d, J=6.5 Hz, 3H) 2.25 (d, J=1.5 Hz, 3H) 2.33 (dd, J=15.8, 8.0 Hz, 1H) 2.44 (dd, J=15.8, 5.0 Hz, 1H) 2.71 (s, 3H) 2.86 (s, 3H) 3.50-3.65 (m, 1H) 7.15 (t, J=9.2 Hz, 1H) 7.55-7.64 (m, 1H) 7.68 (m, J=6.8 Hz, 1H) 7.76 (t, J=7.8 Hz, 1H) 7.84 (d, J=7.8 Hz, 1H) 7.95-8.02 (m, 1H) 8.16-8.21 (m, 1H) 8.34 (t, J=1.5 Hz, 1H) 10.49 (s, 1H).

Compound 40

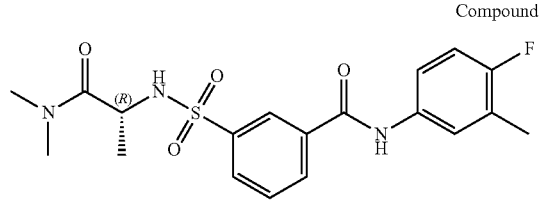

Compound 40 was prepared similarly as described for compound 35 using, D-alanine instead of L-alanine and 2,4,6-tripropyl-1,3,5,2,4,6-trioxatriphosphorinane-2,4,6-trioxide instead of HATU. Method F; Rt: 0.90 min. m/z: 406.1 (M−H)$^−$ Exact mass: 407.1.

Compound 41

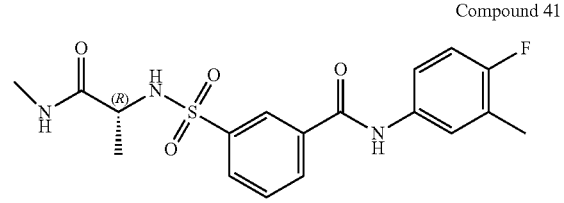

Compound 41 was prepared similarly as compound 40, using methylamine (2M in THF) instead of dimethylamine. Method F; Rt: 0.83 min. m/z: 392.2 (M−H)$^−$ Exact mass: 393.1.

Compound 42

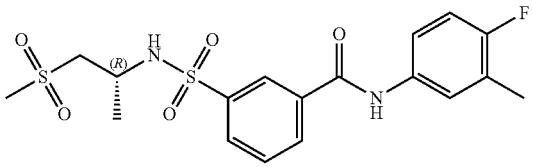

NaSMe (0.213 g, 3.04 mmol) was added to a stirring solution of [(2R)-2-[[3-[(4-fluoro-3-methyl-phenyl)carbamoyl]phenyl]sulfonylamino]propyl]methanesulfonate (0.9 g, 0.00203 mol) in DMF (25 mL). The reaction mixture was stirred at 65° C. under N$_2$-atm for 1 h 30 minutes. The reaction mixture was allowed to reach room temperature, and poured into H$_2$O (125 mL). The product was extracted with EtOAc. The separated organic layer was dried with Na$_2$SO$_4$, filtered off, evaporated, and co-evaporated with toluene, resulting in crude N-(4-fluoro-3-methyl-phenyl)-3-[[(1R)-1-methyl-2-methylsulfanyl-ethyl]sulfamoyl]benzamide (0.76 g). m-CPBA (0.66 g) was added to a stirring solution of crude N-(4-fluoro-3-methyl-phenyl)-3-[[(1R)-1-methyl-2-methylsulfanyl-ethyl]sulfamoyl]benzamide (0.76 g) in CH$_2$Cl$_2$ (15 mL). The reaction mixture was stirred at room temperature for 3 hours. More mCPBA (0.125 g) was added, and the reaction was continued at room temperature for 4 hours. The reaction mixture was quenched with MeOH (15 mL), stirred for 15 minutes, and evaporated. The residue was stirred in CH$_2$Cl$_2$ (10 mL) for 15 minutes, then left standing for 1 hour. The solid was filtered and washed with CH$_2$Cl$_2$ (3×). The filtrate was concentrated in vacuo and the obtained residue was purified by silica gel chromatography heptane-EtOAc 100/0 to 0/100. The desired fractions were combined and evaporated. The white solid residue was stirred in CH$_2$Cl$_2$ (4 mL), filtered off, washed with CH$_2$Cl$_2$ (3×), and dried at 50° C., resulting in compound 42 (0.218 g). Method G; Rt: 1.60 min. m/z: 427.0 (M−H)$^−$ Exact mass: 428.1. $^1$H NMR (400 MHz, DMSO-d$_6$) δ ppm 1.02 (d, J=6.6 Hz, 3H), 2.25 (d, J=1.5 Hz, 3H), 2.99 (s, 3H), 3.17-3.28 (m, 2H), 3.72-3.82 (m, 1H), 7.14 (t, J=9.2 Hz, 1H), 7.56-7.62 (m, 1H), 7.68 (dd, J=7.2, 2.3 Hz, 1H), 7.78 (t, J=7.8 Hz, 1H), 8.01-8.05 (m, 1H), 8.12 (br. s, 1H), 8.20-8.24 (m, 1H), 8.38 (t, J=1.7 Hz, 1H), 10.47 (s, 1H).

Biological Examples—Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxycycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| Compound | HepG2 2.15 EC50 (µM) | HepG2 117 EC50 (µM) | HepG2 4 days CC50 (µM) |
|---|---|---|---|
| 1 | 0.13 | 0.37 | >25 |
| 1a | 0.18 | 0.11 | >25 |
| 1b | 1.85 | 1.57 | >25 |
| 2 | 9.4 | 2.4 | >25 |
| 3 | 7.5 | 1.1 | >25 |
| 4 | 0.28 | 0.32 | >25 |
| 4a | 0.21 | 0.26 | >25 |
| 4b | 0.40 | 0.94 | >25 |
| 5 | 0.24 | 0.84 | >25 |
| 6 | 0.18 | 0.11 | >25 |
| 7 | 0.54 | 0.24 | >25 |
| 8 | 1.4 | 2.8 | >25 |
| 9 | 1.3 | 0.56 | >25 |
| 10 | 0.22 | 0.19 | >25 |
| 10a | 0.10 | 0.14 | >25 |
| 10b | 0.67 | 0.68 | >25 |
| 11 | 0.55 | 0.83 | >25 |
| 12 | 0.65 | 0.82 | >25 |
| 13 | 0.21 | 0.71 | >25 |
| 14 | 0.38 | 0.53 | >25 |
| 15 | 0.22 | 0.32 | >25 |
| 16 | 0.19 | 0.59 | >25 |
| 17 | 0.26 | 0.61 | >25 |
| 18 | 0.20 | 0.19 | >25 |
| 19 | 0.74 | 0.50 | >25 |
| 20 | 0.55 | 0.56 | >25 |
| 21 | 0.17 | 1.71 | >25 |
| 21a | 0.65 | 2.36 | >25 |
| 21b | 0.13 | 0.20 | >25 |
| 22 | 0.55 | 0.50 | >25 |
| 23 | 1.10 | 1.43 | >25 |
| 24 | 0.21 | 1.37 | >25 |
| 25 | 0.25 | 0.57 | >25 |
| 26 | 0.39 | 0.34 | >25 |
| 27 | 1.16 | 0.96 | >25 |
| 28 | 0.27 | 1.41 | >25 |
| 29 | 0.19 | 0.23 | >25 |
| 30 | 0.26 | 0.17 | >25 |
| 31 | 0.48 | 0.47 | >25 |
| 32 | 0.19 | 0.64 | >25 |
| 33 | 0.32 | 0.26 | >25 |
| 34 | 0.54 | 0.64 | >25 |
| 35 | 2.70 | 3.62 | >25 |
| 36 | 0.27 | 0.15 | >25 |
| 37 | 2.68 | 3.03 | >25 |
| 38 | 0.16 | 0.18 | >25 |
| 39 | 1.05 | 0.86 | >25 |
| 40 | 2.28 | 2.66 | >25 |
| 41 | 2.22 | 1.35 | >25 |
| 42 | 0.25 | 0.15 | >25 |

The invention claimed is:

1. A compound of Formula (I)

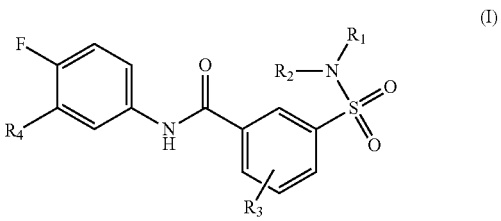

or a stereoisomer or tautomeric form thereof, wherein:
$R_1$ represents hydrogen;
$R_2$ represents $C_1$-$C_8$alkyl substituted with one or more $R_5$,
$R_3$ represents Hydrogen or methyl;
$R_4$ represents methyl;
Each $R_5$ is independently selected from the group consisting of —C≡CH, —CN, —OH, oxo, $C_1$-$C_4$alkyloxy, —C(=O)O—$R_6$, —C(=O)N($R_6$)$_2$, —N($R_6$)$_2$, —NR$_9$C(=O)—$R_6$, NR$_9$C(=O)O—$R_6$ and SO$_2$R$_9$;
Each $R_6$ independently represents hydrogen or $C_1$-$C_3$alkyl;
$R_9$ represents hydrogen or $C_1$-$C_3$alkyl;
or a pharmaceutically acceptable salt or a solvate thereof.

2. The compound according to claim 1, wherein the $C_1$-$C_8$alkyl group as defined in $R_2$ represents a branched $C_2$-$C_6$alkyl.

3. The compound according to claim 1 or 2 of Formula (Ib)

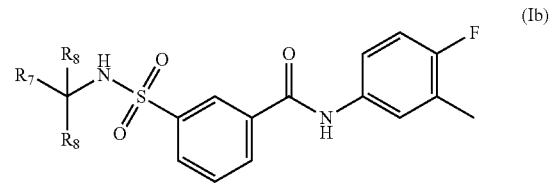

wherein:
$R_7$ is selected from the group consisting of —C≡CH, —CN, —C(=O)O—$R_6$, —C(=O)N($R_6$)$_2$ and $C_1$-$C_4$alkyl optionally substituted with one or more substituents selected from the group consisting of —C≡CH, —CN, —OH, $C_1$-$C_4$alkyloxy, —C(=O)O—$R_6$, —C(=O)N($R_6$)$_2$, —N($R_6$)$_2$, —NHC(=O)—$R_6$ and —NHC(=O)O—$R_6$;
Each $R_6$ independently represents hydrogen or $C_1$-$C_3$alkyl; and wherein
Each $R_8$ independently represents hydrogen or $C_1$-$C_2$alkyl optionally substituted with OH.

4. The compound according to claim 3, wherein $R_7$ is selected from the group consisting of $C_1$-$C_4$alkyl optionally substituted with —C≡CH, —CN, —OH, $C_1$-$C_4$alkyloxy, —C(=O)O—$R_6$, —C(=O)N($R_6$)$_2$, —N($R_6$)$_2$, —NHC(=O)—$R_6$ and —NHC(=O)O—$R_6$.

5. The compound according to claim 1, wherein at least one $R_5$ is —OH.

6. The compound according to claim 3, wherein at least one $R_8$ is $C_1$-$C_2$alkyl substituted with OH.

7. A method of treating an HBV infection in a mammal, comprising administering the compound of claim 1.

8. A pharmaceutical composition comprising a compound according to claim 1, and a pharmaceutically acceptable carrier.

9. A method of treating an HBV infection in a mammal, comprising administering a compound of Formula (I) as defined in claim 1 and another HBV inhibitor.

10. The method of claim 9, wherein said compound of Formula (I) and said another HBV inhibitor are administered simultaneously, separately or sequentially.

* * * * *